(12) United States Patent
Maruyama et al.

(10) Patent No.: US 8,968,980 B2
(45) Date of Patent: Mar. 3, 2015

(54) RADIATION-SENSITIVE RESIN COMPOSITION AND COMPOUND

(75) Inventors: Ken Maruyama, Tokyo (JP); Kota Nishino, Tokyo (JP); Kazuki Kasahara, Tokyo (JP); Hirokazu Sakakibara, Tokyo (JP)

(73) Assignee: JSR Corporation, Tokyo (JP)

( * ) Notice: Subject to any disclaimer, the term of this patent is extended or adjusted under 35 U.S.C. 154(b) by 574 days.

(21) Appl. No.: 13/288,963

(22) Filed: Nov. 4, 2011

(65) Prior Publication Data

US 2012/0045719 A1    Feb. 23, 2012

Related U.S. Application Data

(63) Continuation of application No. PCT/JP2010/058214, filed on May 14, 2010.

(30) Foreign Application Priority Data

May 18, 2009   (JP) .................................. 2009-119960

(51) Int. Cl.
   *G03F 7/004*   (2006.01)
   *G03F 7/039*   (2006.01)
   *C07C 65/10*   (2006.01)

(52) U.S. Cl.
   CPC .............. *C07C 65/10* (2013.01); *G03F 7/0045* (2013.01); *G03F 7/0046* (2013.01); *G03F 7/0397* (2013.01); *Y10S 430/122* (2013.01); *Y10S 430/126* (2013.01)
   USPC .......... 430/270.1; 430/921; 430/925; 560/143

(58) Field of Classification Search
   CPC ........ C07C 65/00; C07C 65/01; C07C 65/10; G03F 7/004; G03F 7/028; G03F 7/029; G03F 7/036; G03F 7/0392
   USPC ........ 562/400, 405; 560/143; 430/270.1, 326, 430/921, 922, 925
   See application file for complete search history.

(56) References Cited

U.S. PATENT DOCUMENTS

| 4,705,860 | A | * | 11/1987 | Ohlendorf et al. ............ 546/347 |
| 4,822,718 | A |   | 4/1989  | Latham et al. |
| 4,828,765 | A | * | 5/1989  | Ohlendorf et al. ............ 562/477 |
| 4,876,165 | A |   | 10/1989 | Brewer et al. |
| 4,910,021 | A |   | 3/1990  | Davis et al. |
| 4,910,122 | A |   | 3/1990  | Arnold et al. |
| 5,403,695 | A |   | 4/1995  | Hayase et al. |
| 5,580,702 | A |   | 12/1996 | Hayase et al. |
| 5,674,648 | A |   | 10/1997 | Brewer et al. |
| 5,744,537 | A |   | 4/1998  | Brunsvold et al. |
| 6,057,080 | A |   | 5/2000  | Brunsvold et al. |
| 6,136,500 | A |   | 10/2000 | Kobayashi et al. |
| 2004/0047905 | A1 | * | 3/2004 | Padlo ............................. 424/465 |

FOREIGN PATENT DOCUMENTS

| JP | 6-12452 B2 |   | 5/1984 |
| JP | 59-169889  | * | 9/1984 |
| JP | 62-195324  |   | 8/1987 |
| JP | 05-181279  |   | 7/1993 |
| JP | 05-188598  |   | 7/1993 |
| JP | 05-323590  |   | 12/1993 |
| JP | 11-125907  |   | 5/1999 |
| JP | 2001-166478|   | 6/2001 |
| JP | 2005-274647|   | 10/2005 |
| JP | 2007-297284|   | 11/2007 |
| WO | WO 03/047562 | * | 6/2003 |
| WO | WO 2008/066011 | * | 6/2008 |

OTHER PUBLICATIONS

Machine translation of the abstract of JP 59-169889, published on Sep. 25, 2009.*
Machine translation of WO 2008/066011, published on Jun. 5, 2008.*
International Search Report for International Application No. PCT/2010/058214, Aug. 3, 2010.
Japanese Office Action for related application No. 2011-514394, mailed May 20, 2014, 2 pages.
Buwalda et al., "Wormlike Micellar and Vesicular Phases in Aqueous Solutions of Single-Tailed Surfactants with Aromatic Counterions", University of Groningen, Langmuir, Jun. 1, 2000, vol. 16, No. 17, pp. 6780-6786, Groningen, Netherlands.

* cited by examiner

*Primary Examiner* — Anca Eoff
(74) *Attorney, Agent, or Firm* — Oblon, Spivak, McClelland, Maier & Neustadt, L.L.P.

(57) ABSTRACT

A radiation-sensitive resin composition includes an acid-dissociable group-containing resin, and a compound shown by the following general formula (1).

$$M^+Z^- \quad (1)$$

$$(R^1)_n \underset{\underset{O}{\|}}{\overset{OH}{\longleftarrow}} O^- \quad (2)$$

wherein $Z^-$ represents a monovalent anion shown by a general formula (2), $M^+$ represents a monovalent onium cation, $R^1$ represents a linear or branched alkyl group having 1 to 12 carbon atoms substituted or unsubstantiated with a fluorine atom, or a linear or branched alkoxy group having 1 to 12 carbon atoms, and n is 1 or 2.

7 Claims, 1 Drawing Sheet

RADIATION-SENSITIVE RESIN COMPOSITION AND COMPOUND

CROSS-REFERENCES TO RELATED APPLICATIONS

The present application is a continuation application of International Application No. PCT/JP2010/058214, filed May 14, 2010, which claims priority under 35 U.S.C. §119 to Japanese Patent Application No. 2009-119960, filed May 18, 2009. The contents of these applications are incorporated herein by reference in their entirety.

BACKGROUND OF THE INVENTION

1. Field of the Invention

The invention relates to a radiation-sensitive resin composition and a compound.

2. Discussion of the Background

A semiconductor device (e.g., IC and LSI) production process utilizes microfabrication by means of lithography using a photoresist composition. Along with an increase in the degree of integration of integrated circuits, it has become necessary to form a sub-micron or quarter-micron fine pattern. Therefore, i-lines, KrF excimer laser light, or ArF excimer laser light having a short exposure wavelength has been used instead of g-lines. Lithography that utilizes electron beams, X-rays, or EUV light instead of excimer laser light has also been developed.

Lithography that utilizes EUV light is considered to be next-generation or third-generation patterning technology, and requires a positive-tone resist that exhibits high sensitivity and high resolution. In particular, it is very important to achieve an increase in sensitivity in order to reduce the wafer processing time. However, when increasing the sensitivity of a positive-tone resist used for EUV light, a deterioration in resolution and nano edge roughness occurs. Therefore, development of a resist that achieves high sensitivity, high resolution, and low nano edge roughness has been strongly desired. Note that the term "nano edge roughness" refers to a phenomenon in which the edge of the resist pattern irregularly changes with respect to the substrate in the direction perpendicular to the line direction due to the properties of the resist, so that a difference occurs between the design dimensions and the actual pattern dimensions when viewed from above. The difference from the design dimensions is transferred by etching using the resist as a mask, and causes a deterioration in electrical properties. As a result, a decrease in yield occurs. In particular, it is very important to reduce the nano edge roughness when forming a fine pattern having a line width of 32 nm or less using EUV light. High sensitivity, high resolution, an excellent pattern shape, and low nano edge roughness have a trade-off relationship. It is very important to achieve these properties at the same time.

KrF excimer laser resist technology has been mainly applied to an EUV positive-tone resist. For example, Japanese Patent Application Publication (KOKAI) No. 2001-166478 discloses a radiation-sensitive resin composition that includes a copolymer of 4-hydroxystyrene and 2-methyl-2-adamantyl acrylate. Japanese Patent Application Publication (KOKAI) No. 5-323590 discloses a radiation-sensitive resin composition that utilizes two types of photoacid generator. Japanese Patent Application Publication (KOKAI) No. 5-181279 discloses a radiation-sensitive resin composition that includes a photoacid generator that generates a strong acid and a photoacid generator that generates a weak acid. Japanese Patent Application Publication (KOKAI) No. 11-125907 discloses a radiation-sensitive resin composition that includes a compound that generates a carboxylic acid having a boiling point of 150° C. or more, and a compound that generates an acid other than a carboxylic acid.

SUMMARY OF THE INVENTION

According to one aspect of the present invention, a radiation-sensitive resin composition includes an acid-dissociable group-containing resin and a compound shown by a general formula (1).

$Z^-$ represents a monovalent anion shown by a general formula (2), and $M^+$ represents a monovalent onium cation.

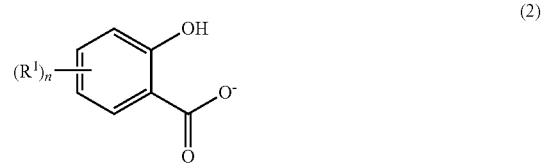

$R^1$ represents a linear or branched alkyl group having 1 to 12 carbon atoms substituted or unsubstituted with a fluorine atom, or a linear or branched alkoxy group having 1 to 12 carbon atoms, and n is 1 or 2.

According to another aspect of the present invention, a compound is shown by a general formula (1).

$Z^-$ represents a monovalent anion shown by a general formula (2), and $M^+$ represents a monovalent onium cation.

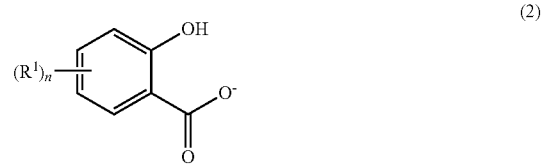

$R^1$ represents a linear or branched alkyl group having 1 to 12 carbon atoms substituted or unsubstituted with a fluorine atom, or a linear or branched alkoxy group having 1 to 12 carbon atoms, and n is 1 or 2.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
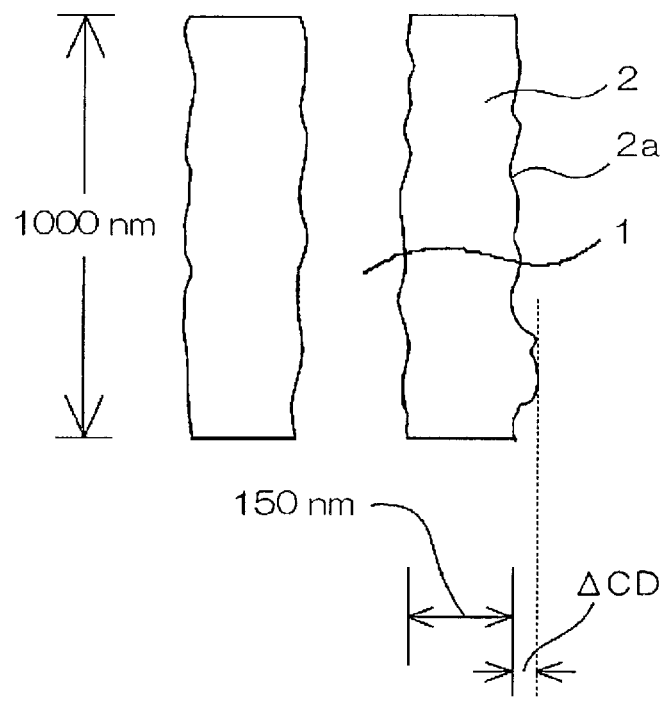
FIG. 1 is a plan view schematically showing a line pattern.

Several embodiments of the invention provide the following radiation-sensitive resin composition and compound.

[1] A radiation-sensitive resin composition including (A) an acid-dissociable group-containing resin (hereinafter may be referred to as "resin (A)"), and (C) a compound shown by a general formula (1) (hereinafter may be referred to as "carboxylic acid generator (C)"), $$M^+Z^- \quad (1)$$

wherein $Z^-$ represents a monovalent anion shown by the following general formula (2), and $M^-$ represents a monovalent onium cation,

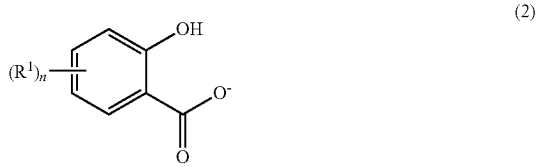

(2)

wherein $R^1$ represents a linear or branched alkyl group having 1 to 12 carbon atoms that may be substituted with a fluorine atom, or a linear or branched alkoxy group having 1 to 12 carbon atoms, and n is 1 or 2.

[2] The radiation-sensitive resin composition according to [1], further including (B) a photoacid generator that generates an acid having a pKa of 2 or less upon exposure to radiation (hereinafter may be referred to as "acid generator (B)").

[3] The radiation-sensitive resin composition according to [2], wherein the photoacid generator (B) is a sulfonic acid generator that generates a sulfonic acid upon exposure to radiation.

[4] The radiation-sensitive resin composition according to any one of [1] to [3], wherein the acid-dissociable group-containing resin (A) includes at least one repeating unit selected from the group consisting of a repeating unit shown by a general formula (3) (hereinafter may be referred to as "repeating unit (2)"), a repeating unit shown by a general formula (4) (hereinafter may be referred to as "repeating unit (3)"), and a repeating unit shown by a general formula (5) (hereinafter may be referred to as "repeating unit (4)"),

(3)

wherein $R^2$ represents a hydrogen atom or a methyl group, $R^3$ represents a hydrogen atom, a linear or branched alkyl group having 1 to 12 carbon atoms, or a linear or branched alkoxy group having 1 to 12 carbon atoms, i is an integer from 0 to 3, and j is an integer from 0 to 3,

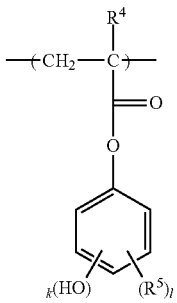

(4)

wherein $R^4$ represents a hydrogen atom or a methyl group, $R^5$ represents a hydrogen atom, a linear or branched alkyl group having 1 to 12 carbon atoms, or a linear or branched alkoxy group having 1 to 12 carbon atoms, k is an integer from 1 to 3, and l is an integer from 0 to 3,

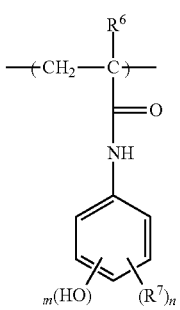

(5)

wherein $R^6$ represents a hydrogen atom or a methyl group, $R^7$ represents a hydrogen atom, a linear or branched alkyl group having 1 to 12 carbon atoms, or a linear or branched alkoxy group having 1 to 12 carbon atoms, m is an integer from 1 to 3, and n is an integer from 0 to 3.

[5] The radiation-sensitive resin composition according to any one of [1] to [4], wherein the acid-dissociable group-containing resin (A) includes a repeating unit shown by a general formula (6),

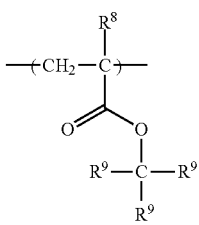

(6)

wherein $R^8$ represents a hydrogen atom, a methyl group, a trifluoromethyl group, or a hydroxymethyl group, and $R^9$ individually represent a monovalent alicyclic hydrocarbon group having 4 to 20 carbon atoms, a derivative thereof, or a linear or branched alkyl group having 1 to 4 carbon atoms, provided that two of $R^9$ may bond to each other to form a divalent alicyclic hydrocarbon group or a derivative thereof together with the carbon atom bonded thereto.

[6] The radiation-sensitive resin composition according to [5], wherein the acid-dissociable group-containing resin (A) further includes at least one of a repeating unit shown by a general formula (L-1) (hereinafter may be referred to as "repeating unit (L)") and a repeating unit shown by a general formula (C-1) (hereinafter may be referred to as "repeating unit (C)"),

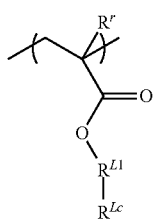

(L-1)

wherein $R^r$ represents a hydrogen atom, a methyl group, or a trifluoromethyl group, $R^{L1}$ represents a single bond or a divalent linking group, and $R^{Lc}$ represents a monovalent organic group having a lactone structure,

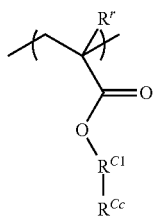

(C-1)

wherein $R^r$ represents a hydrogen atom, a methyl group, or a trifluoromethyl group, $R^{C1}$ represents a single bond or a divalent linking group, and $R^{Cc}$ represents a monovalent organic group having a cyclic carbonate structure.

[7] A compound shown by a general formula (1), $$M^+Z^- \quad (1)$$

wherein $Z^-$ represents a monovalent anion shown by a general formula (2), and $M^+$ represents a monovalent onium cation,

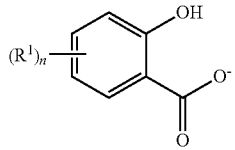

(2)

wherein $R^1$ represents a linear or branched alkyl group having 1 to 12 carbon atoms that may be substituted with a fluorine atom, or a linear or branched alkoxy group having 1 to 12 carbon atoms, and n is 1 or 2.

The above radiation-sensitive resin composition can produce a chemically-amplified positive-tone resist film that effectively responds to (extreme) deep ultraviolet rays (e.g., KrF excimer laser light, ArF excimer laser light, or EUV), X-rays (e.g., synchrotron radiation), or electron beams, exhibits low nano edge roughness, excellent sensitivity, and excellent resolution, and can stably and accurately produce a fine pattern.

The above compound may suitably used for the above radiation-sensitive resin composition.

The embodiments will now be described with reference to the accompanying drawings, wherein like reference numerals designate corresponding or identical elements throughout the various drawings.

Exemplary embodiments of the invention are described below. Note that the invention is not limited to the following exemplary embodiments. It should be understood that various modifications, improvements, and the like may be made of the following exemplary embodiments without departing from the scope of the invention based on the knowledge of a person skilled in the art.

I. Radiation-Sensitive Resin Composition

A radiation-sensitive resin composition according to one embodiment of the invention includes the resin (A) and the carboxylic acid generator (C), and may further include the acid generator (B).

1. Acid-Dissociable Group-Containing Resin (A)

The resin (A) includes an acid-dissociable group-containing repeating unit. The resin (A) is normally insoluble or scarcely soluble in alkali, but becomes readily soluble in alkali due to an acid. The expression "insoluble or scarcely soluble in alkali" means that a film (thickness: 100 nm) that is formed only of the resin (A) has a thickness equal to or more than 50% of the initial thickness when developed under alkaline development conditions employed when forming a resist pattern using a resist film that is formed of a radiation-sensitive resin composition that includes the resin (A).

A radiation-sensitive resin composition that includes the resin (A) exhibits excellent sensitivity. A chemically-amplified positive-tone resist film that effectively responds to electron beams or extreme ultraviolet rays during a lithographic process, exhibits low roughness, excellent sensitivity, and excellent resolution, and can accurately and stably form a fine pattern can be formed using such a radiation-sensitive resin composition.

(1) Component

The resin (A) preferably includes at least one repeating unit (hereinafter may be referred to as "repeating unit (1)") selected from a repeating unit shown by the general formula (6) and a repeating unit shown by the following general formula (7).

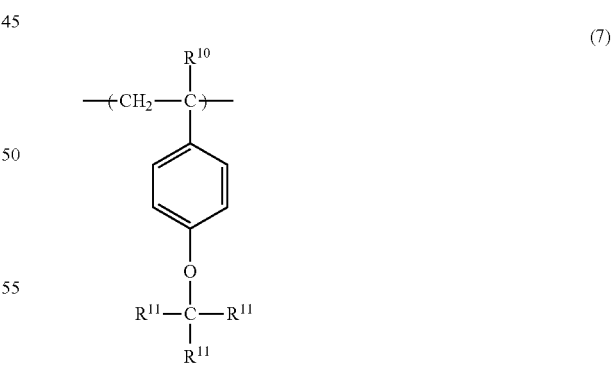

(7)

wherein $R^{10}$ represents a hydrogen atom, a methyl group, a trifluoromethyl group, or a hydroxymethyl group, and $R^{11}$ individually represent a monovalent alicyclic hydrocarbon group having 4 to 20 carbon atoms, a derivative thereof, or a linear or branched alkyl group having 1 to 4 carbon atoms, provided that two of $R^{11}$ may bond to each other to form a divalent alicyclic hydrocarbon group or a derivative thereof together with the carbon atom bonded thereto.

Examples of the linear or branched alkyl group having 1 to 4 carbon atoms represented by $R^9$ in the general formula (6) include a methyl group, an ethyl group, an n-propyl group, an i-propyl group, an n-butyl group, a 2-methylpropyl group, a 1-methylpropyl group, a t-butyl group, and the like. Examples of the monovalent alicyclic hydrocarbon group having 4 to 20 carbon atoms include a group that includes an alicyclic ring derived from a cycloalkane such as norbornane, tricyclodecane, tetracyclododecane, adamantane, cyclobutane, cyclopentane, cyclohexane, cycloheptane, or cyclooctane; a group obtained by substituting such a group with at least one linear, branched, or cyclic alkyl group having 1 to 4 carbon atoms (e.g., methyl group, ethyl group, n-propyl group, i-propyl group, n-butyl group, 2-methylpropyl group, 1-methylpropyl group, or t-butyl group); and the like. Examples of the divalent alicyclic hydrocarbon group or a derivative thereof formed by two of $R^9$ together with the carbon atom bonded thereto include a group that includes an alicyclic ring derived from norbornane, tricyclodecane, tetracyclododecane, adamantane, cyclopentane, or cyclohexane, and a group obtained by substituting such a group with a linear, branched, or cyclic alkyl group having 1 to 4 carbon atoms, and the like.

Specific examples of the group represented by $R^{11}$ in the general formula (7) include the groups mentioned above as specific examples of the group represented by $R^9$ in the general formula (6).

It is preferable that the repeating unit (1) be any of repeating units shown by the following general formulas (6-1) to (6-7) and (7-1). Among these, repeating units shown by the general formulas (6-2) to (6-4) are particularly preferable.

(6-1)

(6-2) 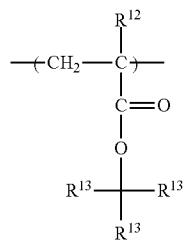

(6-3) 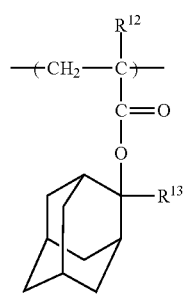

(6-4) 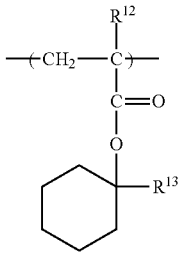

(6-5) 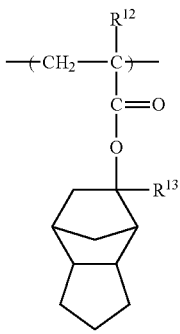

(6-6) 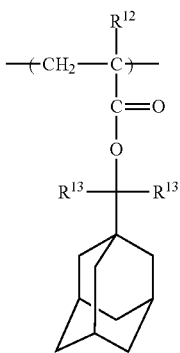

(6-7) 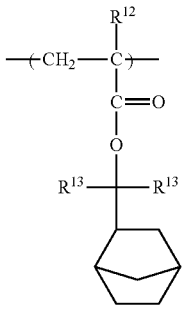

(7-1) 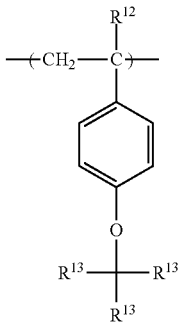

wherein $R^{12}$ represents a hydrogen atom, a methyl group, a trifluoromethyl group, or a hydroxymethyl group, and $R^{13}$ individually represent a linear or branched alkyl group having 1 to 4 carbon atoms.

The resin (A) may include only one type of repeating unit (1), or may include two or more types of repeating unit (1).

The resin (A) may include only the repeating unit (1), but preferably further includes at least one repeating unit selected from the group consisting of the repeating unit (2), the repeating unit (3), and the repeating unit (4) in addition to the repeating unit (1).

The repeating unit (2) is shown by the general formula (3). Examples of the linear or branched alkyl group having 1 to 12 carbon atoms represented by $R^3$ in the general formula (3) include a methyl group, an ethyl group, an n-propyl group, an i-propyl group, an n-butyl group, a 2-methylpropyl group, a 1-methylpropyl group, a t-butyl group, and the like. Examples of the linear or branched alkoxy group having 1 to 12 carbon atoms include a methoxy group, an ethoxy group, an n-propoxy group, an i-propoxy group, an n-butoxy group, a 1-methylpropoxy group, a 2-methylpropoxy group, a t-butoxy group, and the like. Among these, a methyl group, an ethyl group, an n-butyl group, and a t-butyl group are preferable.

i in the general formula (3) is an integer from 0 to 3, and preferably 1 or 2. j is an integer from 0 to 3, and preferably an integer from 0 to 2.

Specific examples of the repeating unit (2) shown by the general formula (3) include the repeating units shown by the following formulas (3-1) to (3-4), and the like. When the resin (A) includes the repeating unit (2), the resin (A) may include only one type of repeating unit (2), or may include two or more types of repeating unit (2).

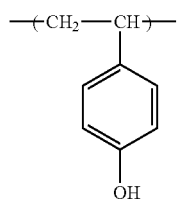

(3-1)

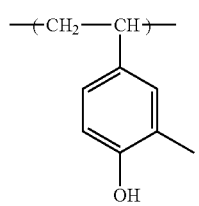

(3-2)

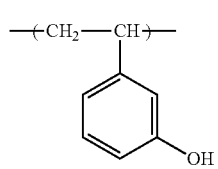

(3-3)

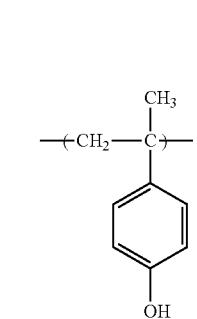

(3-4)

The repeating unit (3) is shown by the general formula (4). Examples of the linear or branched alkyl group having 1 to 12 carbon atoms and the linear or branched alkoxy group having 1 to 12 carbon atoms represented by $R^5$ in the general formula (4) include the groups mentioned above in connection with $R^3$ in the general formula (3).

k in the general formula (4) is an integer from 1 to 3, and preferably 1 or 2. l is an integer from 0 to 3, and preferably 0 or 1.

Specific examples of the repeating unit (3) include the repeating units shown by the following formulas (4-1) and (4-2), and the like. When the resin (A) includes the repeating unit (3), the resin (A) may include only one type of repeating unit (3), or may include two or more types of repeating unit (3).

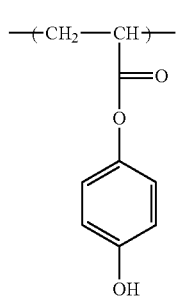

(4-1)

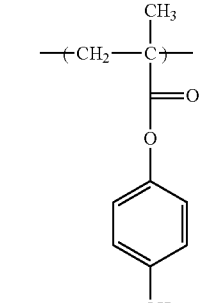

(4-2)

The repeating unit (4) is shown by the general formula (5). Examples of the linear or branched alkyl group having 1 to 12 carbon atoms and the linear or branched alkoxy group having 1 to 12 carbon atoms represented by $R^7$ in the general formula (5) include the groups mentioned above in connection with $R^3$ in the general formula (3).

m in the general formula (5) is an integer from 1 to 3, and preferably 1 or 2. n is an integer from 0 to 3, and preferably 0 or 1.

Specific examples of the repeating unit (4) include the repeating units shown by the following formulas (5-1) and (5-2), and the like. When the resin (A) includes the repeating unit (4), the resin (A) may include only one type of repeating unit (4), or may include two or more types of repeating unit (4).

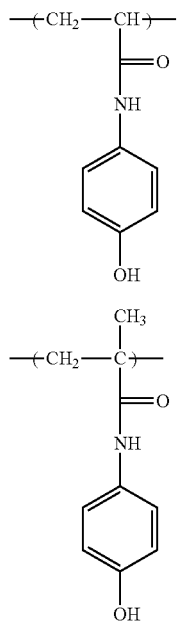

(5-1)

(5-2)

A polymer that includes the repeating unit shown by any of the formulas (3-1) to (3-3) may be obtained by polymerizing the corresponding hydroxystyrene derivative as a monomer. A polymer that includes the repeating unit shown by any of the formulas (3-1) to (3-3) may also be obtained by polymerizing a compound that produces the corresponding hydroxystyrene derivative via hydrolysis as a monomer. The monomers used to produce the repeating units shown by the formulas (3-1) to (3-3) are preferably p-acetoxystyrene, p-(1-ethoxyethoxy)styrene, and the like. When using such a monomer, a polymer that includes the repeating unit shown by any of the formulas (3-1) to (3-3) may be obtained by polymerizing the monomer, and hydrolyzing the side chain of the resulting polymer.

A polymer that includes the repeating unit shown by any of the formulas (3-4), (4-1), (4-2), (5-1), and (5-2) may be obtained by polymerizing the corresponding monomer. The monomers used to produce the repeating units shown by the formulas (3-4), (4-1), (4-2), (5-1), and (5-2) are preferably p-isopropenylphenol, 4-hydroxyphenyl acrylate, 4-hydroxyphenyl methacrylate, N-(4-hydroxyphenyl)acrylamide, N-(4-hydroxyphenyl)methacrylamide, and the like.

The resin (A) may include a repeating unit derived from a non-acid-dissociable compound (hereinafter may be referred to as "repeating unit (5)").

Examples of the repeating unit (5) include a repeating unit derived from styrene, α-methylstyrene, 4-methylstyrene, 2-methylstyrene, 3-methylstyrene, isobornyl acrylate, tricyclodecanyl(meth)acrylate, tetracyclododecenyl(meth)acrylate, or the like, the repeating unit (L), the repeating unit (C), and the like. Among these, a repeating unit derived from styrene, α-methylstyrene, 4-methylstyrene, 2-methylstyrene, 3-methylstyrene, tricyclodecanyl acrylate, or the like, the repeating unit (L), and the repeating unit (C) are preferable. When the resin (A) includes the repeating unit (5), the resin (A) may include only one type of repeating unit (5), or may include two or more types of repeating unit (5). The term "(meth)acrylate" used herein refers to "acrylate" or "methacrylate".

Specific examples of the monovalent organic group having a lactone structure represented by $R^{Lc}$ in the general formula (L-1) include groups shown by the following general formulas (Lc-1) to (Lc-6).

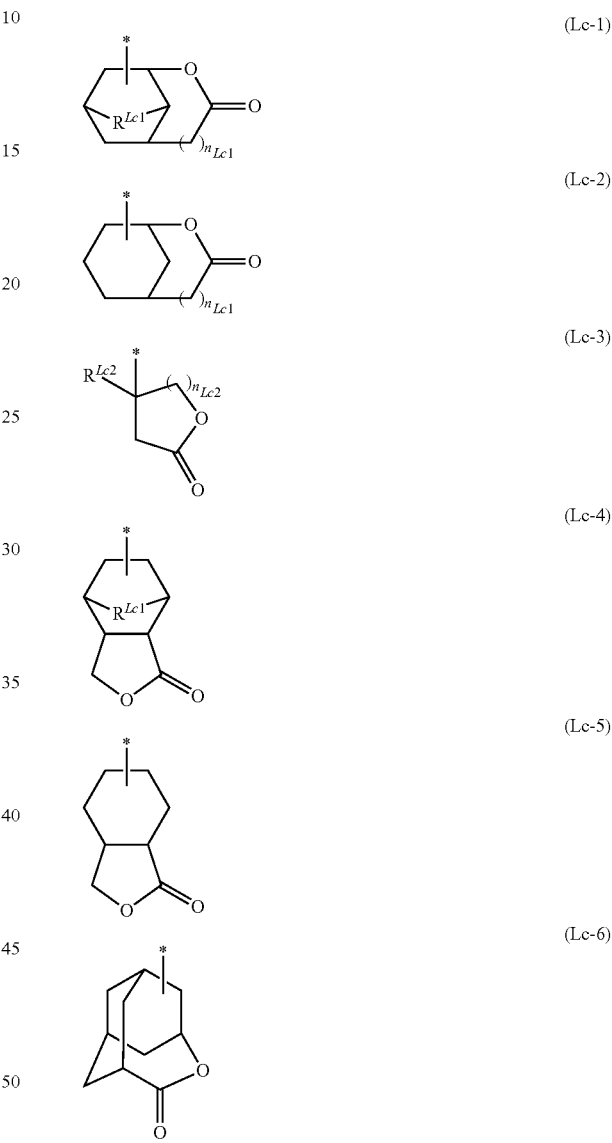

wherein $R^{Lc1}$ represents an oxygen atom or a methylene group, $R^{Lc2}$ represents a hydrogen atom or an alkyl group having 1 to 4 carbon atoms, $n_{Lc1}$ is 0 or 1, $n_{Lc2}$ is an integer from 0 to 3, and the symbol "*" represents a bonding hand bonded to $R^{L1}$ in the general formula (L-1). Note that groups shown by the general formulas (Lc-1) to (Lc-6) may include a substituent.

Specific examples of the repeating unit (L) include the repeating units disclosed in paragraphs 0054 to 0057 of Japanese Patent Application Publication (KOKAI) No. 2007-304537, the repeating units disclosed in paragraphs 0086 to 0087 of Japanese Patent Application Publication (KOKAI) No. 2008-088343, and repeating units shown by the following general formulas (L-1a) to (L-1l). Note that R in the general formulas (L-1a) to (L-1l) represents a hydrogen atom, a methyl group, or a trifluoromethyl group.
(L-1a)
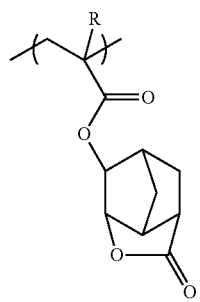
(L-1b)
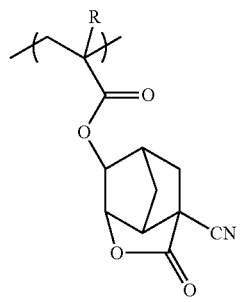
(L-1c)
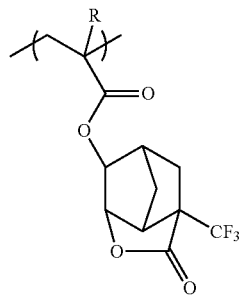
(L-1d)
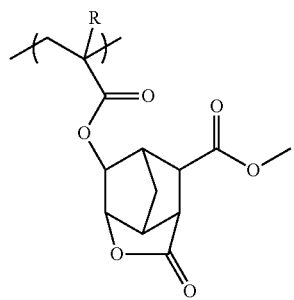
-continued
(L-1e)
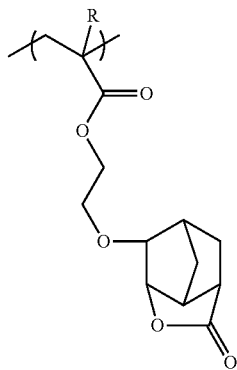
(L-1f)
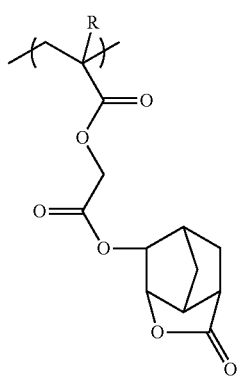
(L-1g)
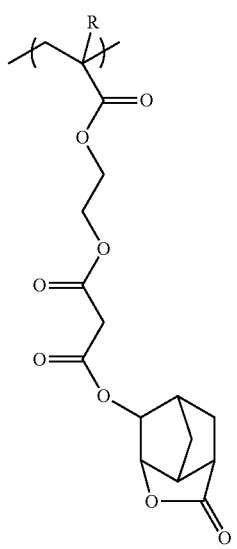
(L-1h)
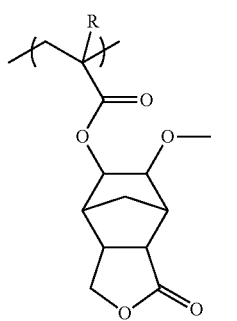

(L-1i)
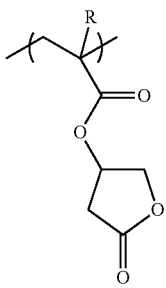

(L-1j)
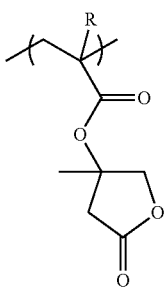

(L-1k)
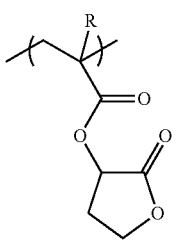

(L-1l)
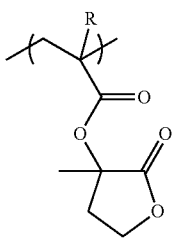

Specific examples of the monovalent organic group having a cyclic carbonate structure represented by $R^{Cc}$ in the general formula (C-1) include groups shown by the following general formulas (Cc-1) and (Cc-2).

(Cc-1)
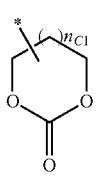

(Cc-2)
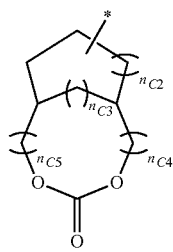

wherein $n_{C1}$ is an integer from 0 to 2, $n_{C2}$ to $n_{C5}$ are individually an integer from 0 to 2, and the symbol "*" represents a bonding hand bonded to $R^{C1}$ in the general formula (C-1). Note that groups shown by the general formulas (Cc-1) and (Cc-2) may include a substituent.

Specific examples of groups shown by the general formulas (Cc-1) and (Cc-2) include the groups shown by the following formulas (Cc-11) and (Cc-21). Note that the symbol "*" in the formulas (Cc-11) and (Cc-21) represents a bonding hand bonded to $R^{C1}$ in the general formula (C-1).

(Cc-11)
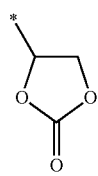

(Cc-12)
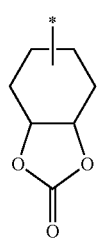

Specific examples of the repeating unit (C) that includes the group shown by the formula (Cc-11) or (Cc-21) include repeating units shown by the following general formulas (C-1a) to (C-1j). Note that R in the general formulas (C-1a) to (C-1j) represents a hydrogen atom, a methyl group, or a trifluoromethyl group.

(C-1a)
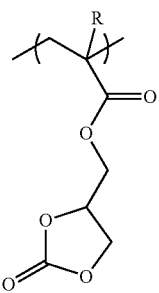

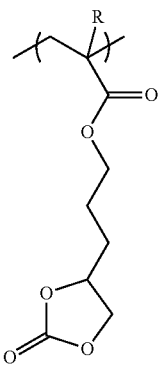 (C-1b)
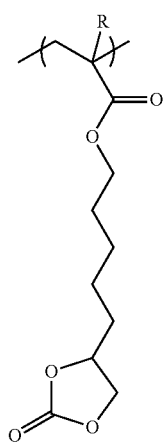 (C-1c)
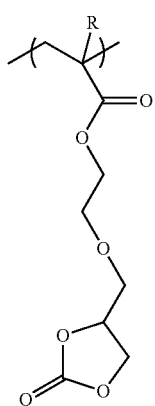 (C-1d)
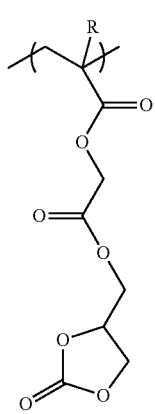 (C-1e)
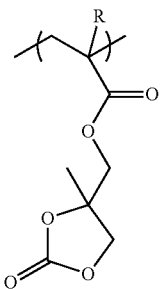 (C-1f)
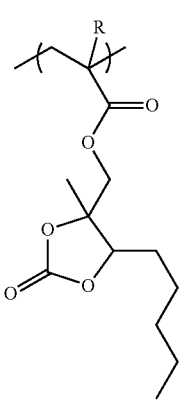 (C-1g)
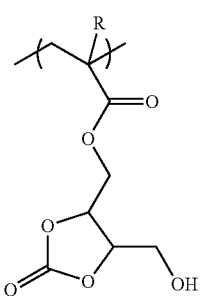 (C-1h)
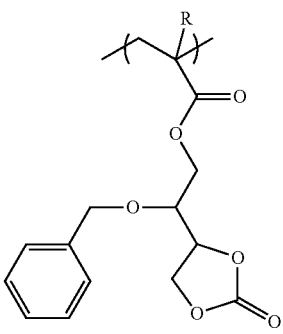 (C-1i)

-continued

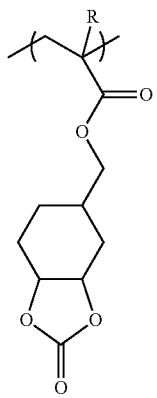

(C-1j)

The content of the repeating unit (1) in the resin (A) is preferably 1 mol % or more, more preferably 20 to 70 mol %, and still more preferably 20 to 60 mol %, based on the total content (=100 mol %) of the repeating units included in the resin (A). If the content of the repeating unit (1) is 1 mol % or more, the resulting resist film (pattern) exhibits low nano edge roughness.

The total content of the repeating units (2) to (4) in the resin (A) is preferably 1 to 95 mol %, more preferably 10 to 95 mol %, and still more preferably 40 to 80 mol %, based on the total content (=100 mol %) of the repeating units included in the resin (A). If the total content of the repeating units (2) to (4) exceeds 95 mol %, the resulting resist film (pattern) may exhibit increased nano edge roughness.

The total content of the repeating units (1) to (4) in the resin (A) is preferably 10 mol % or more, more preferably 40 to 100 mol %, and still more preferably 50 to 100 mol %, based on the total content (=100 mol %) of the repeating units included in the resin (A). If the total content of the repeating units (1) to (4) is 10 mol % or more, the resulting resist film (pattern) exhibits low nano edge roughness.

The content of the repeating unit (5) in the resin (A) is normally 60 mol % or less, and preferably 50 mol % or less, based on the total content (=100 mol %) of the repeating units included in the resin (A). If the content of the repeating unit (5) is 60 mol % or less, the resulting resist film (pattern) exhibits excellent resolution and low nano edge roughness in a well-balanced manner.

(2) Production Method

The resin (A) may be produced by an arbitrary method. For example, the resin (A) may be produced by radical polymerization or anionic polymerization. The hydroxystyrene unit (side chain) of the repeating units (2) to (4) may be obtained by hydrolyzing the resulting polymer (e.g., acetoxy group) in an organic solvent in the presence of a base or an acid.

For example, radical polymerization may be implemented by stirring and heating the monomers (e.g., a monomer that produces the repeating unit (1)) in an appropriate organic solvent under a nitrogen atmosphere in the presence of a radical initiator.

Examples of the radical initiator include azo compounds such as 2,2'-azobisisobutylonitrile, dimethyl-2,2'-azobisisobutyrate, 2,2'-azobis(2,4-dimethylvaleronitrile), 2,2'-azobis(4-methoxy-2,4-dimethylvaleronitrile), 2,2'-azobismethylbutyronitrile, 2,2'-azobiscyclohexanecarbonitrile, cyanomethylethylazoformamide, 2,2'-azobis(methyl 2,4-dimethylpropanate), and 2,2'-azobiscyanovaleric acid; organic peroxides such as benzoyl peroxide, lauroyl peroxide, 1,1'-bis(t-butylperoxy)cyclohexane, 3,5,5-trimethylhexanoyl peroxide, and t-butyl peroxy-2-ethylhexanoate; hydrogen peroxide; and the like. A polymerization promoter such as 2,2,6,6-tetramethyl-1-piperidinyloxy, iodine, a mercaptan, or a styrene dimer may optionally be used for radical polymerization.

The radical polymerization temperature is appropriately selected (e.g., 50 to 200° C.) depending on the type of radical initiator and the like. When using an azo initiator or a peroxide initiator, the radical polymerization temperature is preferably determined so that the half-life of the radical initiator is about 10 minutes to about 30 hours, and more preferably about 30 minutes to about 10 hours. The reaction time is determined depending on the type of radical initiator and the reaction temperature, but is preferably determined so that 50% or more of the radical initiator is consumed (normally about 0.5 to about 24 hours).

Anionic polymerization may be implemented by stirring the monomers (e.g., a monomer that produces the repeating unit (1)) at a given temperature in an appropriate organic solvent under a nitrogen atmosphere in the presence of an anionic initiator, for example.

Examples of the anionic initiator include organic alkali metals such as n-butyllithium, s-butyllithium, t-butyllithium, ethyllithium, ethylsodium, 1,1-diphenylhexyllithium, 1,1-diphenyl-3-methylpentyllithium, and the like.

The anionic polymerization temperature is appropriately selected depending on the type of anionic initiator and the like. When using an alkyllithium as the anionic initiator, the anionic polymerization temperature is preferably −100 to 50° C., and more preferably −78 to 30° C. The reaction time is determined depending on the type of anionic initiator and the reaction temperature, but is preferably determined so that 50% or more of the anionic initiator is consumed (normally about 0.5 to about 24 hours).

Note that the resin (A) may be produced by heating the monomers without using an initiator, or may be produced by cationic polymerization.

Examples of the acid used when introducing the hydroxystyrene unit by hydrolyzing the side chain of the polymer (A) include organic acids such as p-toluenesulfonic acid, a hydrate thereof, methanesulfonic acid, trifluoromethanesulfonic acid, malonic acid, oxalic acid, and 1,1,1-trifluoroacetic acid; inorganic acids such as sulfuric acid, hydrochloric acid, phosphoric acid, and hydrobromic acid; salts such as pyridinium p-toluenesulfonate, ammonium p-toluenesulfonate, and 4-methylpyridinium p-toluenesulfonate; and the like. Examples of the base include inorganic bases such as potassium hydroxide, sodium hydroxide, sodium carbonate, and potassium carbonate; organic bases such as triethylamine, N-methyl-2-pyrrolidone, piperidine, and tetramethylammonium hydroxide; and the like.

Examples of the organic solvent used for polymerization or hydrolysis include ketones such as acetone, methyl ethyl ketone, and methyl amyl ketone; ethers such as diethyl ether and tetrahydrofuran (THF); alcohols such as methanol, ethanol, and propanol; aliphatic hydrocarbons such as hexane, heptane, and octane; aromatic hydrocarbons such as benzene, toluene, and xylene; alkyl halides such as chloroform, bromoform, methylene chloride, methylene bromide, and carbon tetrachloride; esters such as ethyl acetate, butyl acetate, ethyl lactate, propylene glycol monomethyl ether, propylene glycol monomethyl ether acetate, and cellosolve; aprotic polar solvents such as dimethylformamide, dimethyl sulfoxide, and hexamethylphosphoroamide; and the like. Among these, acetone, methyl amyl ketone, methyl ethyl ketone, tetrahydrofuran, methanol, ethanol, propanol, ethyl acetate, butyl acetate, ethyl lactate, propylene glycol monomethyl ether, propylene glycol monomethyl ether acetate, and the like are preferable.

(3) Properties

The polystyrene-reduced weight average molecular weight (hereinafter may be referred to as "Mw") of the resin (A) determined by gel permeation chromatography (GPC) is preferably 3000 to 100,000, more preferably 3000 to 40,000, and still more preferably 3000 to 25,000. The ratio (Mw/Mn) of the Mw to the polystyrene-reduced number average molecular weight (hereinafter may be referred to as "Mn") of the resin (A) determined by GPC is normally 1 to 5, preferably 1 to 3, and more preferably 1 to 2.5.

2. Photoacid Generator (B)

The acid generator (B) generates an acid having a pKa of 2 or less in a resist film formed using the radiation-sensitive resin composition when applying electron beams, radiation, or the like to the resist film during a lithographic process. The pKa of the acid generated by the acid generator (B) upon exposure to radiation is preferably 0 or less. The lower limit of the pKa of the acid generated by the acid generator (B) upon exposure to radiation is not particularly limited, but is normally −15 or more.

The acid generated by the acid generator (B) upon exposure to radiation and having a pKa of 2 or less causes the acid-dissociable group in the resin (A) included in the radiation-sensitive resin composition to dissociate (causes elimination of the protecting group), so that the resin (A) becomes alkali-soluble. As a result, the exposed area of the resist film is readily dissolved in an alkaline developer, so that a positive-tone resist pattern is formed. The acid generator (B) is preferably a sulfonic acid generator that generates a sulfonic acid upon exposure to radiation.

The acid generator (B) is not particularly limited as long as the acid generator (B) has the above function. Examples of the acid generator (B) include a sulfonic acid generator shown by the following general formula (9), and the like.

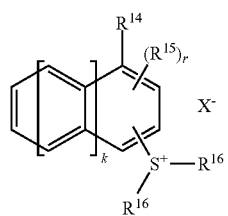

(9)

wherein $R^{14}$ represents a hydrogen atom, a fluorine atom, a hydroxyl group, a linear or branched alkyl group having 1 to 10 carbon atoms, a linear or branched alkoxy group having 1 to 10 carbon atoms, or a linear or branched alkoxycarbonyl group having 2 to 11 carbon atoms, $R^{15}$ represents a linear or branched alkyl group having 1 to 10 carbon atoms, a linear or branched alkoxy group having 1 to 10 carbon atoms, or a linear, branched, or cyclic alkylsulfonyl group having 1 to 10 carbon atoms, $R^{16}$ individually represent a linear or branched alkyl group having 1 to 10 carbon atoms, a substituted or unsubstituted phenyl group, or a substituted or unsubstituted naphthyl group, provided that $R^{16}$ may bond to each other to form a substituted or unsubstituted divalent group having 2 to 10 carbon atoms, k is an integer from 0 to 2, r is an integer from 0 to 10, $X^-$ represents an anion shown by the following general formula (10): $R^{17}C_nF_{2n}SO_3^-$ or the following general formula (11): $R^{18}SO_3^-$, $R^{17}$ and $R^{18}$ represent a fluorine atom, a substituted or unsubstituted hydrocarbon group having 1 to 12 carbon atoms, or a substituted or unsubstituted alicyclic hydrocarbon group having 3 to 20 carbon atoms, and n is an integer from 1 to 10.

Examples of the linear or branched alkyl group having 1 to 10 carbon atoms represented by $R^{14}$ in the general formula (9) include a methyl group, an ethyl group, an n-butyl group, a 2-methylpropyl group, a 1-methylpropyl group, a t-butyl group, an n-pentyl group, and the like. Among these, a methyl group, an ethyl group, an n-butyl group, and a t-butyl group are preferable. Specific examples of the linear or branched alkyl group having 1 to 10 carbon atoms represented by $R^{15}$ and $R^{16}$ include the groups mentioned above in connection with $R^{14}$.

Examples of the linear or branched alkoxy group having 1 to 10 carbon atoms include a methoxy group, an ethoxy group, an n-propoxy group, an i-propoxy group, an n-butoxy group, a 1-methylpropoxy group, a 2-methylpropoxy group, a t-butoxy group, and the like. Among these, a methoxy group, an ethoxy group, an n-propoxy group, and an n-butoxy group are preferable. Specific examples of the linear or branched alkoxy group having 1 to 10 carbon atoms represented by $R^{15}$ include the groups mentioned above in connection with $R^{14}$.

Examples of the linear or branched alkoxylcarbonyl group having 2 to 11 carbon atoms include a methoxycarbonyl group, an ethoxycarbonyl group, an n-propoxycarbonyl group, an i-propoxycarbonyl group, an n-butoxycarbonyl group, a 2-methylpropoxycarbonyl group, a 1-methylpropoxycarbonyl group, a t-butoxycarbonyl group, and the like. Among these, a methoxycarbonyl group, an ethoxycarbonyl group, and an n-butoxycarbonyl group are preferable.

Examples of the linear, branched, or cyclic alkylsulfonyl group having 1 to 10 carbon atoms represented by $R^{15}$ include a methylsulfonyl group, an ethylsulfonyl group, an n-propylsulfonyl group, an n-butylsulfonyl group, a t-butylsulfonyl group, a cyclopentylsulfonyl group, a cyclohexylsulfonyl group, and the like. Among these, a methylsulfonyl group, an ethylsulfonyl group, an n-propylsulfonyl group, an n-butylsulfonyl group, a cyclopentylsulfonyl group, and a cyclohexylsulfonyl group are preferable.

r is an integer from 0 to 10, and preferably an integer from 0 to 2.

Examples of the substituted or unsubstituted phenyl group represented by $R^{16}$ include a phenyl group; a phenyl group substituted with a linear, branched, or cyclic alkyl group having 1 to 10 carbon atoms, such as a 4-ethylphenyl group, a 4-t-butylphenyl group, a 4-cyclohexylphenyl group, and a 4-fluorophenyl group; a group obtained by substituting a phenyl group or the above alkyl-substituted phenyl group with at least one group (e.g., alkoxy group, alkoxyalkyl group, alkoxycarbonyl group, alkoxycarbonyloxy group, hydroxyl group, carboxyl group, cyano group, or nitro group); and the like.

Examples of the alkoxy group as a substituent for a phenyl group or the alkyl-substituted phenyl group include linear, branched, or cyclic alkoxy groups having 1 to 20 carbon atoms, such as a methoxy group, an ethoxy group, an n-propoxy group, a t-butoxy group, a cyclopentyloxy group, and a cyclohexyloxy group, and the like.

Examples of the alkoxyalkyl group include linear, branched, or cyclic alkoxyalkyl groups having 2 to 21 carbon atoms, such as a methoxymethyl group, an ethoxymethyl group, a 1-methoxyethyl group, a 2-methoxyethyl group, a 1-ethoxyethyl group, and a 2-ethoxyethyl group, and the like.

Examples of the alkoxycarbonyl group include linear, branched, or cyclic alkoxycarbonyl groups having 2 to 21 carbon atoms, such as a methoxycarbonyl group, an ethoxycarbonyl group, an n-propoxycarbonyl group, an i-propoxycarbonyl group, an n-butoxycarbonyl group, a 2-methylpropoxycarbonyl group, a 1-methylpropoxycarbonyl group, a t-butoxycarbonyl group, a cyclopentyloxycarbonyl group, and a cyclohexyloxycarbonyl group, and the like.

Examples of the alkoxycarbonyloxy group include linear, branched, or cyclic alkoxycarbonyloxy groups having 2 to 21 carbon atoms, such as a methoxycarbonyloxy group, an ethoxycarbonyloxy group, an n-propoxycarbonyloxy group, an i-propoxycarbonyloxy group, an n-butoxycarbonyloxy group, a t-butoxycarbonyloxy group, and a cyclopentyloxycarbonyloxy group, and a cyclohexyloxycarbonyloxy group, and the like.

Among these substituted or unsubstituted phenyl groups, a phenyl group, a 4-cyclohexylphenyl group, a 4-t-butylphenyl group, a 4-methoxyphenyl group, and a 4-t-butoxyphenyl group are preferable.

Examples of the substituted or unsubstituted naphthyl group represented by $R^{16}$ include naphthyl groups substituted or unsubstituted with a linear, branched, or cyclic alkyl group having 1 to 10 carbon atoms, such as a 1-naphthyl group, a 2-methyl-1-naphthyl group, a 3-methyl-1-naphthyl group, a 4-methyl-1-naphthyl group, a 5-methyl-1-naphthyl group, a 6-methyl-1-naphthyl group, a 7-methyl-1-naphthyl group, a 8-methyl-1-naphthyl group, a 2,3-dimethyl-1-naphthyl group, a 2,4-dimethyl-1-naphthyl group, a 2,5-dimethyl-1-naphthyl group, a 2,6-dimethyl-1-naphthyl group, a 2,7-dimethyl-1-naphthyl group, a 2,8-dimethyl-1-naphthyl group, a 3,4-dimethyl-1-naphthyl group, a 3,5-dimethyl-1-naphthyl group, a 3,6-dimethyl-1-naphthyl group, a 3,7-dimethyl-1-naphthyl group, a 3,8-dimethyl-1-naphthyl group, a 4,5-dimethyl-1-naphthyl group, a 5,8-dimethyl-1-naphthyl group, a 4-ethyl-1-naphthyl group, a 2-naphthyl group, a 1-methyl-2-naphthyl group, a 3-methyl-2-naphthyl group, and a 4-methyl-2-naphthyl group; groups obtained by substituting a naphthyl group or the alkyl-substituted naphthyl groups with at least one group such as a hydroxyl group, a carboxyl group, a cyano group, a nitro group, an alkoxyl group, an alkoxyalkyl group, an alkoxycarbonyl group, or an alkoxycarbonyloxy group; and the like.

Specific examples of a substituent for a naphthyl group and the alkyl-substituted naphthyl group include the substituents mentioned above in connection with a phenyl group and the alkyl-substituted phenyl group.

Among the substituted or unsubstituted naphthyl groups, a 1-naphthyl group, a 1-(4-methoxynaphthyl) group, a 1-(4-ethoxynaphthyl) group, a 1-(4-n-propoxynaphthyl) group, a 1-(4-n-butoxynaphthyl) group, a 2-(7-methoxynaphthyl) group, a 2-(7-ethoxynaphthyl) group, a 2-(7-n-propoxynaphthyl) group, and a 2-(7-n-butoxynaphthyl) group are preferable.

The substituted or unsubstituted divalent group having 2 to 10 carbon atoms formed by the two $R^{16}$ is preferably a group that forms a 5 or 6-membered ring (more preferably a 5-membered ring (i.e., tetrahydrothiophene ring)) together with the sulfur cation included in the compound shown by the general formula (9).

Examples of a substituent for the divalent group having 2 to 10 carbon atoms include a hydroxyl group, a carboxyl group, a cyano group, a nitro group, an alkoxy group, an alkoxyalkyl group, an alkoxycarbonyl group, an alkoxycarbonyloxy group, and the like.

$R^{16}$ preferably represent a methyl group, an ethyl group, a phenyl group, a 4-methoxyphenyl group, or a 1-naphthyl group, or bond to each other to form a divalent group having a tetrahydrothiophene ring structure together with the sulfur cation.

When $X^-$ represents an anion shown by the general formula (10): $R^{17}C_nF_{2n}SO_3^-$, "—$C_nF_{2n}$—" is a perfluoroalkylene group having n carbon atoms. The perfluoroalkylene group may be linear or branched. n is preferably 1, 2, 4, or 8.

The substituted or unsubstituted hydrocarbon group having 1 to 12 carbon atoms represented by $R^{17}$ is preferably an alkyl group having 1 to 12 carbon atoms, a cycloalkyl group, or a bridged alicyclic hydrocarbon group. The substituted or unsubstituted hydrocarbon group having 1 to 12 carbon atoms represented by $R^{17}$ is more preferably a methyl group, an ethyl group, an n-propyl group, an i-propyl group, an n-butyl group, a 2-ethylhexyl group, an n-nonyl group, an n-decyl group, a norbornyl group, a norbornylmethyl group, a hydroxynorbornyl group, or an adamantyl group. Specific examples of the substituted or unsubstituted hydrocarbon group having 1 to 12 carbon atoms represented by $R^{18}$ in the general formula (11) include the groups mentioned above in connection with $R^{17}$.

The anion represented by $X^-$ is preferably a trifluoromethanesulfonate anion, a perfluoro-n-butanesulfonate anion, a perfluoro-n-octanesulfonate anion, a 2-bicyclo[2.2.1]hept-2-yl-1,1,2,2-tetrafluoroethanesulfonate anion, or a 2-bicyclo[2.2.1]hept-2-yl-1,1-difluoroethanesulfonate anion.

Specific examples of the compound shown by the general formula (9) include triphenylsulfonium trifluoromethanesulfonate, tri-tert-butylphenylsulfonium trifluoromethanesulfonate, 4-cyclohexylphenyl-diphenylsulfonium trifluoromethanesulfonate, 4-methanesulfonylphenyl-diphenylsulfonium trifluoromethanesulfonate, 1-(3,5-dimethyl-4-hydroxyphenyl)tetrahydrothiophenium trifluoromethanesulfonate, 1-(4-n-butoxynaphthyl)tetrahydrothiophenium trifluoromethanesulfonate, triphenylsulfonium perfluoro-n-butanesulfonate, tri-tert-butylphenylsulfonium perfluoro-n-butanesulfonate, 4-cyclohexylphenyl-diphenylsulfonium perfluoro-n-butanesulfonate, 4-methanesulfonylphenyl-diphenylsulfonium perfluoro-n-butanesulfonate, 1-(3,5-dimethyl-4-hydroxyphenyl)tetrahydrothiophenium perfluoro-n-butanesulfonate, 1-(4-n-butoxynaphthyl)tetrahydrothiophenium perfluoro-n-butanesulfonate, triphenylsulfonium perfluoro-n-octanesulfonate, tri-tert-butylphenylsulfonium perfluoro-n-octanesulfonate, 4-cyclohexylphenyl-diphenylsulfonium perfluoro-n-octanesulfonate, 4-methanesulfonylphenyl-diphenylsulfonium perfluoro-n-octanesulfonate, 1-(3,5-dimethyl-4-hydroxyphenyl)tetrahydrothiophenium perfluoro-n-octanesulfonate, 1-(4-n-butoxynaphthyl)tetrahydrothiophenium perfluoro-n-octanesulfonate, triphenylsulfonium 2-(bicyclo[2.2.1]hept-2'-yl)-1,1,2,2-tetrafluoroethanesulfonate, tri-tert-butylphenylsulfonium 2-(bicyclo[2.2.1]hept-2'-yl)-1,1,2,2-tetrafluoroethanesulfonate, 4-cyclohexylphenyldiphenylsulfonium 2-(bicyclo[2.2.1]hept-2'-yl)-1,1,2,2-tetrafluoroethanesulfonate, 4-methanesulfonylphenyldiphenylsulfonium 2-(bicyclo[2.2.1]hept-2'-yl)-1,1,2,2-tetrafluoroethanesulfonate, 1-(3,5-dimethyl-4-hydroxyphenyl)tetrahydrothiophenium 2-(bicyclo[2.2.1]hept-2'-yl)-1,1,2,2-tetrafluoroethanesulfonate, 1-(4-n-butoxynaphthyl)tetrahydrothiophenium 2-(bicyclo[2.2.1]hept-2'-yl)-1,1,2,2-tetrafluoroethanesulfonate, triphenylsulfonium 2-(bicyclo[2.2.1]hept-2'-yl)-1,1-difluoroethanesulfonate, tri-tert-butylphenylsulfonium 2-(bicyclo[2.2.1]hept-2'-yl)-1,1-difluoroethanesulfonate, 4-cyclohexylphenyldiphenylsulfonium 2-(bicyclo[2.2.1]hept-2'-yl)-

1,1-difluoroethanesulfonate, 4-methanesulfonylphenyldiphenylsulfonium 2-(bicyclo[2.2.1]hept-2'-yl)-1,1-difluoroethanesulfonate, 1-(3,5-dimethyl-4-hydroxyphenyl)tetrahydrothiophenium 2-(bicyclo[2.2.1]hept-2'-yl)-1,1-difluoroethanesulfonate, 1-(4-n-butoxynaphthyl)tetrahydrothiophenium 2-(bicyclo[2.2.1]hept-2'-yl)-1,1-difluoroethanesulfonate, and the like. Note that the acid generator (B) may include only one type of compound shown by the general formula (9), or may include two or more types of compound shown by the general formula (9).

The acid generator (B) is preferably used in an amount of 0.1 to 40 parts by mass, and more preferably 10 to 35 parts by mass, based on 100 parts by mass of the resin (A). If the amount of the acid generator (B) is within the above range, the resulting resist film exhibits sufficient sensitivity and developability. If the amount of the acid generator (B) is less than 0.1 parts by mass, the resulting resist film may exhibit decreased sensitivity and developability. If the amount of the acid generator (B) exceeds 40 parts by mass, a rectangular resist pattern may not be obtained due to a decrease in transparency to radiation.

3. Carboxylic Acid Generator (C)

The carboxylic acid generator (C) normally exhibits basicity. The carboxylic acid generator (C) generates a carboxylic acid when applying electron beams, radiation, or the like to the resist film during a lithographic process, and loses basicity. The carboxylic acid generator (C) is a compound shown by the general formula (1).

Examples of the linear or the branched alkyl group having 1 to 12 carbon atoms that may be substituted with a fluorine atom, and the linear or branched alkoxy group having 1 to 12 carbon atoms represented by $R^1$ in the general formula (2) include a methyl group, an ethyl group, an n-propyl group, an i-propyl group, an n-butyl group, a 2-methylpropyl group, a 1-methylpropyl group, a t-butyl group, a methoxy group, an ethoxy group, an n-propoxy group, an i-propoxy group, an n-butoxy group, a 2-methylpropoxy group, a 1-methylpropoxy group, a t-butoxy group, a trifluoromethyl group, a pentafluoroethyl group, a heptafluoropropyl group, a nonafluorobutyl group, a dodecafluoropentyl group, a perfluorooctyl group, and the like. Among these, a methyl group, a trifluoromethyl group, a pentafluoroethyl group, a heptafluoropropyl group, and a nonafluorobutyl group are preferable, and a trifluoromethyl group is particularly preferable. n is 1 or 2, and preferably 1.

$M^+$ in the general formula (1) represents a monovalent onium cation (preferably a sulfonium cation or an iodonium cation). $M^+$ particularly preferably represents a cation shown by the following general formula (12).

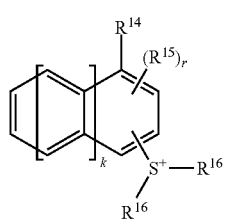

(12)

wherein $R^{14}$ is the same as $R^{14}$ in the general formula (9), $R^{15}$ is the same as $R^{15}$ in the general formula (9), $R^{16}$ is the same as $R^{16}$ in the general formula (9), r is the same as r in the general formula (9), and k is the same as k in the general formula (9).

Specific examples of a compound shown by the general formula (1) include the compounds shown by the following formulas (1-1) and (1-2), and the like.

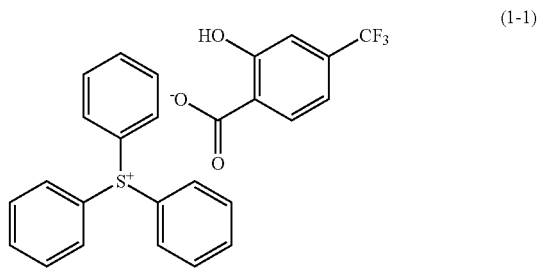

(1-1)

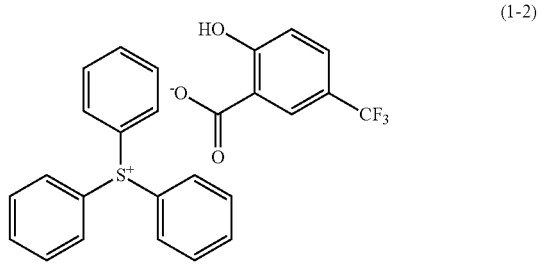

(1-2)

Synthesis Method

The carboxylic acid generator (C) may be synthesized by an arbitrary method. For example, the carboxylic acid generator (C) may be synthesized by reacting a compound shown by the following general formula (13) with sodium carbonate in an aqueous solution to obtain a compound shown by the following general formula (14), and reacting the compound with a halide of the desired onium cation $M^+$ (e.g., $M^+Br^-$) in an aqueous solution (see the following reaction formula).

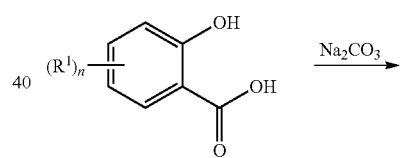

(13)

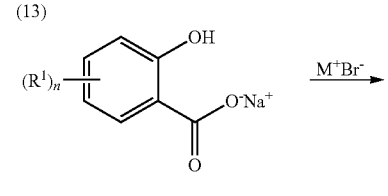

(14)

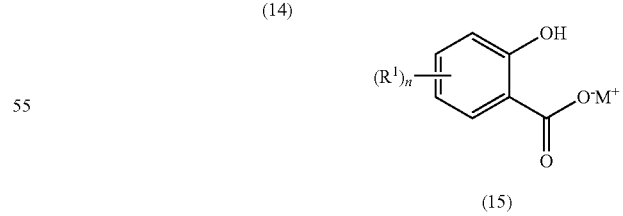

(15)

wherein $R^1$ represents a linear or branched alkyl group having 1 to 12 carbon atoms that may be substituted with a fluorine atom, or a linear or branched alkoxy group having 1 to 12 carbon atoms, and n is 1 or 2, and $M^+$ represents a monovalent onium cation.

The carboxylic acid generator (C) is preferably used in an amount of 30 parts by mass or less, and more preferably 2 to 25 parts by mass, based on 100 parts by mass of the resin (A). If the amount of the carboxylic acid generator (C) exceeds 30 parts by mass, the resulting resist film may exhibit low resolution. If the amount of the carboxylic acid generator (C) is less than 2 parts by mass, the resulting resist film may also exhibit low resolution.

4. Acid Diffusion Controller (D)

The radiation-sensitive resin composition according to one embodiment of the invention preferably further includes (D) an acid diffusion controller. The acid diffusion controller (D) controls a phenomenon wherein an acid generated by the acid generator (B) upon exposure is diffused in the resist film, and suppresses undesired chemical reactions in the unexposed area.

The acid diffusion controller (D) improves the storage stability of the resulting radiation-sensitive resin composition and the resolution of the resist film formed using the radiation-sensitive resin composition. Moreover, the acid diffusion controller (D) prevents a change in line width of the resist pattern due to a change in post-exposure delay (PED) from exposure to post-exposure bake, so that a radiation-sensitive resin composition that exhibits excellent process stability can be obtained.

Examples of the acid diffusion controller (D) include nitrogen-containing organic compounds and photosensitive basic compounds. Examples of the nitrogen-containing organic compounds include a compound shown by the following general formula (16) (hereinafter referred to as "nitrogen-containing compound (i)"), a compound that includes two nitrogen atoms in the molecule (hereinafter referred to as "nitrogen-containing compound (ii)"), a polyamino compound or a polymer that includes three or more nitrogen atoms (hereinafter collectively referred to as "nitrogen-containing compound (iii)"), an amide group-containing compound, a urea compound, a nitrogen-containing heterocyclic compound, and the like.

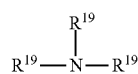

(16)

wherein $R^{19}$ individually represent a hydrogen atom, a substituted or unsubstituted linear, branched, or cyclic alkyl group, a substituted or unsubstituted aryl group, or a substituted or unsubstituted aralkyl group.

Examples of the nitrogen-containing compound (i) include mono(cyclo)alkylamines such as n-hexylamine, n-heptylamine, n-octylamine, n-nonylamine, n-decylamine, and cyclohexylamine; di(cyclo)alkylamines such as di-n-butylamine, di-n-pentylamine, di-n-hexylamine, di-n-heptylamine, di-n-octylamine, di-n-nonylamine, di-n-decylamine, cyclohexylmethylamine, and dicyclohexylamine; tri(cyclo)alkylamines such as triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, cyclohexyldimethylamine, methyldicyclohexylamine, and tricyclohexylamine; substituted alkylamines such as triethanolamine; and aromatic amines such as aniline, N-methylaniline, N,N-dimethylaniline, 2-methylaniline, 3-methylaniline, 4-methylaniline, 4-nitroaniline, diphenylamine, triphenylamine, naphthylamine, 2,4,6-tri-tert-butyl-N-methylaniline, N-phenyldiethanolamine, 2,6-diisopropylaniline, 2-(4-aminophenyl)-2-(3-hydroxyphenyl)propane, and 2-(4-aminophenyl)-2-(3-hydroxyphenyl)propane.

Examples of the nitrogen-containing compound (ii) include ethylenediamine, N,N,N',N'-tetramethylethylenediamine, tetramethylenediamine, hexamethylenediamine, 4,4'-diaminodiphenylmethane, 4,4'-diamino diphenyl ether, 4,4'-diaminobenzophenone, 4,4'-diaminodiphenylamine, 2,2-bis(4-aminophenyl)propane, 2-(3-aminophenyl)-2-(4-aminophenyl)propane, 1,4-bis[1-(4-aminophenyl)-1-methylethyl]benzene, 1,3-bis[1-(4-aminophenyl)-1-methylethyl]benzene, bis(2-dimethylaminoethyl)ether, bis(2-diethylaminoethyl)ether, 1-(2-hydroxyethyl)-2-imidazolizinone, 2-quinoxalinol, N,N,N',N'-tetrakis(2-hydroxypropyl)ethylenediamine, and the like.

Examples of the nitrogen-containing compound (iii) include polyethyleneimine, polyallylamine, poly(2-dimethylaminoethylacrylamide), and the like.

Examples of the amide group-containing compound include N-t-butoxycarbonyl group-containing amino compounds such as N-t-butoxycarbonyl di-n-octylamine, N-t-butoxycarbonyl di-n-nonylamine, N-t-butoxycarbonyl di-n-decylamine, N-t-butoxycarbonyl dicyclohexylamine, N-t-butoxycarbonyl-1-adamantylamine, N-t-butoxycarbonyl-2-adamantylamine, N-t-butoxycarbonyl-N-methyl-1-adamantylamine, (S)-(–)-1-(t-butoxycarbonyl)-2-pyrrolidine methanol, (R)-(+)-1-(t-butoxycarbonyl)-2-pyrrolidine methanol, N-t-butoxycarbonyl-4-hydroxypiperidine, N-t-butoxycarbonylpyrrolidine, N-t-butoxycarbonylpiperazine, N,N-di-t-butoxycarbonyl-1-adamantylamine, N,N-di-t-butoxycarbonyl-N-methyl-1-adamantylamine, N-t-butoxycarbonyl-4,4'-diaminodiphenylmethane, N,N'-di-t-butoxycarbonylhexamethylenediamine, N,N,N'N'-tetra-t-butoxycarbonylhexamethylenediamine, N,N'-di-t-butoxycarbonyl-1,7-diaminoheptane, N,N'-di-t-butoxycarbonyl-1,8-diaminonooctane, N,N'-di-t-butoxycarbonyl-1,9-diaminononane, N,N'-di-t-butoxycarbonyl-1,10-diaminodecane, N,N'-di-t-butoxycarbonyl-1,12-diaminododecane, N,N'-di-t-butoxycarbonyl-4,4'-diaminodiphenylmethane, N-t-butoxycarbonylbenzimidazole, N-t-butoxycarbonyl-2-methylbenzimidazole, and N-t-butoxycarbonyl-2-phenylbenzimidazole; formamide, N-methylformamide, N,N-dimethylformamide, acetamide, N-methylacetamide, N,N-dimethylacetamide, propionamide, benzamide, pyrrolidone, N-methylpyrrolidone, N-acetyl-1-adamantylamine, tris(2-hydroxyethyl)isocyanuric acid, and the like.

Examples of the urea compound include urea, methylurea, 1,1-dimethylurea, 1,3-dimethylurea, 1,1,3,3-tetramethylurea, 1,3-diphenylurea, tri-n-butylthiourea, and the like.

Examples of the nitrogen-containing heterocyclic compound include imidazoles such as imidazole, 4-methylimidazole, 4-methyl-2-phenylimidazole, benzimidazole, 2-phenylbenzimidazole, 1-benzyl-2-methylimidazole, and 1-benzyl-2-methyl-1H-imidazole; pyridines such as pyridine, 2-methylpyridine, 4-methylpyridine, 2-ethylpyridine, 4-ethylpyridine, 2-phenylpyridine, 4-phenylpyridine, 2-methyl-4-phenylpyridine, nicotine, nicotinic acid, nicotinic acid amide, quinoline, 4-hydroxyquinoline, 8-oxyquinoline, acridine, and 2,2':6',2''-terpyridine; piperazines such as piperazine and 1-(2-hydroxyethyl)piperazine; and pyrazine, pyrazole, pyridazine, quinoxaline, purine, pyrrolidine, piperidine, piperidineethanol, 3-piperidino-1,2-propanediol, morpholine, 4-methylmorpholine, 1-(4-morpholinyl)ethanol, 4-acetylmorpholine, 3-(N-morpholino)-1,2-propanediol, 1,4-dimethylpiperazine, 1,4-diazabicyclo[2.2.2]octane, and the like.

These acid diffusion controllers (D) may be used either individually or in combination.

The acid diffusion controller (D) is preferably used in an amount of 15 parts by mass or less, more preferably 0.001 to 10 parts by mass, and still more preferably 0.005 to 5 parts by mass, based on 100 parts by mass of the resin (A). If the amount of the acid diffusion controller (D) exceeds 15 parts by mass, the sensitivity of the resulting resist film or the developability of the exposed area may decrease. If the amount of the acid diffusion controller (D) is less than 0.001 parts by mass, the pattern shape or the dimensional accuracy of the resulting resist film may deteriorate depending on the process conditions.

5. Other Components

The radiation-sensitive resin composition according to one embodiment of the invention is preferably prepared by dissolving the polymer (A), the acid generator (B), and the carboxylic acid generator (C) in a solvent. Specifically, the radiation-sensitive resin composition preferably further includes a solvent. Additives such as a surfactant, a sensitizer, and an aliphatic additive may optionally be added to the radiation-sensitive resin composition.

The solvent is preferably at least one compound selected from the group consisting of linear or branched ketones, cyclic ketones, propylene glycol monoalkyl ether acetates, alkyl 2-hydroxypropionates, alkyl 3-alkoxypropionates, and γ-butyrolactone.

The solvent is preferably used so that the radiation-sensitive resin composition has a total solid content of 1 to 70 mass %, more preferably 1 to 15 mass %, and still more preferably 1 to 10 mass %.

The radiation-sensitive resin composition may be prepared by homogeneously dissolving the polymer (A), the acid generator (B), the carboxylic acid generator (C), and optional components (excluding the solvent) in the solvent so that the total solid content is within the above range. The radiation-sensitive resin composition thus prepared is preferably filtered through a filter having a pore size of about 0.2 μm, for example.

The surfactant improves the applicability, striation, developability, and the like. Examples of the surfactant include nonionic surfactants such as polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate, and polyethylene glycol distearate; commercially available products such as KP341 (manufactured by Shin-Etsu Chemical Co., Ltd.), Polyflow No. 75, Polyflow No. 95 (manufactured by Kyoeisha Chemical Co., Ltd.), EFTOP EF301, EFTOP EF303, EFTOP EF352 (manufactured by JEMCO, Inc.), Megafac F171, Megafac F173 (manufactured by DIC Corporation), Fluorad FC430, Fluorad FC431 (manufactured by Sumitomo 3M Ltd.), Asahi Guard AG710, Surflon S-382, Surflon SC-101, Surflon SC-102, Surflon SC-103, Surflon SC-104, Surflon SC-105, Surflon SC-106 (manufactured by Asahi Glass Co., Ltd.), and the like. These surfactants may be used either individually or in combination. The surfactant is preferably used in an amount of 0.001 to 2 parts by mass based on 100 parts by mass of the resin (A).

The sensitizer absorbs the energy of radiation, and transmits the energy to the acid generator (B) so that the amount of acid generated by the acid generator (B) increases. Specifically, the sensitizer improves the apparent sensitivity of the radiation-sensitive resin composition. Examples of the sensitizer include carbazoles, acetophenones, benzophenones, naphthalenes, phenols, biacetyl, eosine, rose bengal, pyrenes, anthracenes, phenothiazines, and the like. These sensitizers may be used either individually or in combination. The sensitizer is preferably used in an amount of 0.1 to 10 parts by mass based on 100 parts by mass of the resin (A).

A dye or a pigment visualizes the latent image in the exposed area, and reduces the effects of halation during exposure. An adhesion improver improves the adhesion of the resist film to the substrate.

The alicyclic additive further improves the dry etching resistance, the pattern shape, the adhesion to a substrate, and the like. Specific examples of the alicyclic additive include adamantane derivatives such as 1-adamantanecarboxylic acid, 2-adamantanone, t-butyl-1-adamantanecarboxylate, t-butoxycarbonylmethyl 1-adamantanecarboxylate, α-butyrolactone 1-adamantanecarboxylate, di-t-butyl 1,3-adamantanedicarboxylate, t-butyl 1-adamantaneacetate, t-butoxycarbonylmethyl 1-adamantaneacetate, di-t-butyl 1,3-adamantanediacetate, and 2,5-dimethyl-2,5-di(adamantylcarbonyloxy)hexane; deoxycholates such as t-butyl deoxycholate, t-butoxycarbonylmethyl deoxycholate, 2-ethoxyethyl deoxycholate, 2-cyclohexyloxyethyl deoxycholate, 3-oxocyclohexyl deoxycholate, tetrahydropyranyl deoxycholate, and mevalonolactone deoxycholate; lithocholates such as t-butyl lithocholate, t-butoxycarbonylmethyl lithocholate, 2-ethoxyethyl lithocholate, 2-cyclohexyloxyethyl lithocholate, 3-oxocyclohexyl lithocholate, tetrahydropyranyl lithocholate, and mevalonolactone lithocholate; 3-(2-hydroxy-2,2-bis(trifluoromethyl)ethyl)tetracyclo[6.2.1.1$^{3,6}$.0$^{2.7}$]dodecane; and These alicyclic additives may be used either individually or in combination.

The alicyclic additive is preferably used in an amount of 0.5 to 20 parts by mass based on 100 parts by mass of the resin (A). If the amount of the alicyclic additive exceeds 20 parts by mass, the heat resistance of the resulting resist film may decrease.

Examples of further additives include an alkali-soluble polymer, a low-molecular-weight alkali solubility controller that includes an acid-dissociable protecting group, a halation inhibitor, a preservative, an antifoaming agent, and the like.

Formation of Resist Pattern

The radiation-sensitive resin composition according to one embodiment of the invention is useful as a material for forming a chemically-amplified positive-tone resist film. The chemically-amplified positive-tone resist film is designed so that the acid-dissociable group included in the resin (A) dissociates due to an acid generated by the acid generator (B) upon exposure so that the resin (A) becomes alkali-soluble. Specifically, an alkali-soluble area is formed in the resist film. The alkali-soluble area corresponds to the exposed area of the resist. The exposed area can be dissolved and removed using an alkaline developer. A positive-tone resist pattern having a desired shape can thus be formed. The resist pattern-forming process is described in detail below.

First, a resist film is formed using the radiation-sensitive resin composition according to one embodiment of the invention. The radiation-sensitive resin composition may have been filtered through a filter having a pore size of about 0.2 μm after adjusting the total solid content, for example. The radiation-sensitive resin composition is applied to a substrate (e.g., silicon wafer or aluminum-coated wafer) using an appropriate application method (e.g., rotational coating, cast coating, or roll coating) to form a resist film. The resist film may optionally be pre-baked (PB) at about 70 to 160° C. The resist film is then exposed to form a desired resist pattern. Examples of radiation that may be used for exposure include (extreme) deep ultraviolet rays such as KrF excimer laser light (wavelength: 248 nm), ArF excimer laser light (wavelength: 193 nm), EUV (extreme ultraviolet rays, wavelength: 13.5 nm), X-rays such as synchrotron radiation, charged particle rays such as electron beams, and the like. The exposure conditions (e.g., dose) may be appropriately selected depending on the composition of the radiation-sensitive resin composition, the type of additive, and the like. Note that liquid immersion lithography may also be used.

The resist film is preferably subjected to post-exposure bake (PEB) after exposure. PEB ensures smooth dissociation of the acid-dissociable group included in the resin (A). The PEB conditions may be appropriately selected depending on the composition of the radiation-sensitive resin composition. The PEB temperature is preferably 30 to 200° C., and more preferably 50 to 170° C.

In order to bring out the potential of the radiation-sensitive resin composition to a maximum extent, an organic or inorganic anti-reflective film may be formed on the substrate, as disclosed in Japanese Examined Patent Publication (KOKOKU) No. 6-12452 (Japanese Patent Application Publication (KOKAI) No. 59-93448), for example. A protective film may be formed on the resist film so that the resist film is not affected by basic impurities and the like contained in the environmental atmosphere, as disclosed in Japanese Patent Application Publication (KOKAI) No. 5-188598, for example. These methods may be used in combination.

The resist film thus exposed is developed to form a given resist pattern. The developer used for development is preferably an aqueous alkaline solution prepared by dissolving at least one alkaline compound (e.g., sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethylammonium hydroxide, pyrrole, piperidine, choline, 1,8-diazabicyclo-[5.4.0]-7-undecene, or 1,5-diazabicyclo-[4.3.0]-5-nonene) in water.

The concentration of the alkaline aqueous solution is normally 10 mass % or less. If the concentration of the aqueous alkaline solution exceeds 10 mass %, the unexposed area may also be dissolved in the developer. The pH of the developer is preferably 8 to 14, and more preferably 9 to 14.

An organic solvent may be added to the alkaline aqueous solution (developer), for example. Examples of the organic solvent include ketones such as acetone, methyl ethyl ketone, methyl i-butyl ketone, cyclopentanone, cyclohexanone, 3-methylcyclopentanone, and 2,6-dimethylcyclohexanone; alcohols such as methanol, ethanol, n-propyl alcohol, i-propyl alcohol, n-butyl alcohol, t-butyl alcohol, cyclopentanol, cyclohexanol, 1,4-hexanediol, and 1,4-hexanedimethylol; ethers such as tetrahydrofuran and dioxane; esters such as ethyl acetate, n-butyl acetate, and i-amyl acetate; aromatic hydrocarbons such as toluene and xylene; phenol, acetonylacetone, dimethylformamide; and the like. These organic solvents may be used either individually or in combination.

The organic solvent is preferably used in an amount of 100 parts by volume or less based on 100 parts by volume of the alkaline aqueous solution. If the amount of the organic solvent exceeds 100 parts by volume, the exposed area may remain undeveloped due to a decrease in developability. An appropriate amount of a surfactant or the like may also be added to the alkaline aqueous solution (developer). After development using the aqueous alkaline solution (developer), the resist film may be washed with water, and dried.

II. Compound

A compound according to one embodiment of the invention is the compound described in the section entitled "3. Carboxylic acid generator (C)".

EXAMPLES

The invention is further described below by way of examples. Note that the invention is not limited to the following examples. In the examples and comparative examples, the unit "parts" refers to "parts by mass", and the unit "%" refers to "mass %", unless otherwise specified. The property value measuring methods and the property evaluation methods employed in the examples are described below.

Weight Average Molecular Weight (Mw) and Number Average Molecular Weight (Mn)

The weight average molecular weight (Mw) and the number average molecular weight (Mn) of the resin were determined by gel permeation chromatography (GPC) using GPC columns manufactured by Tosoh Corp. (G2000HXL×2, G3000HXL×1, G4000HXL×1) (flow rate: 1.0 ml/min, eluant: tetrahydrofuran, column temperature: 40° C., standard: monodisperse polystyrene). The dispersity (Mw/Mn) was calculated from the measurement results.

$^{13}$C-NMR Analysis

The resin was subjected to $^{13}$C-NMR analysis using a mass spectrometer "JNM-EX270" (manufactured by JEOL Ltd.).

The following evaluation methods were employed in Examples 1 to 5 and Comparative Examples 1 to 3.

Sensitivity (L/S) (μC/cm$^2$)

A dose at which a line-and-space pattern (1L1S) including a line area (width: 150 nm) and a space area (groove) (width: 150 nm) defined by the adjacent line areas was formed at a line width of 1:1 was defined as an optimum dose, and the sensitivity was evaluated based on the optimum dose.

Nano Edge Roughness (nm)

Figure 2:
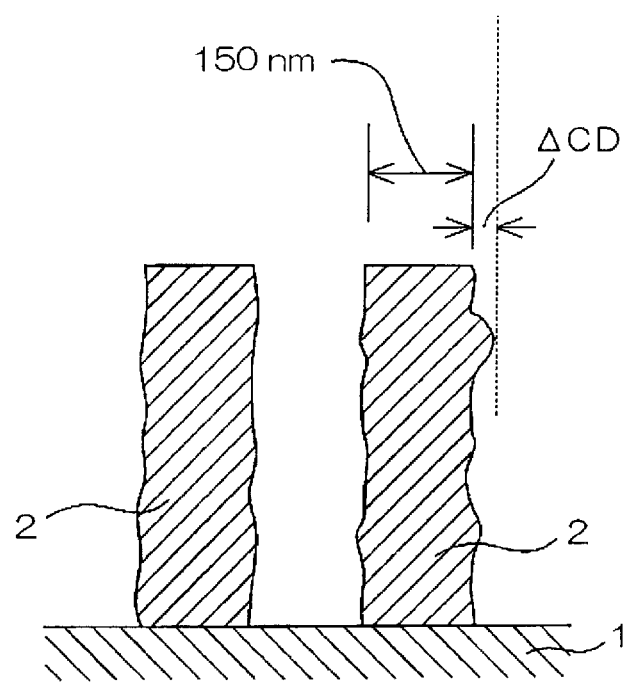
FIG. 2 is a cross-sectional view schematically showing the shape of a line pattern.

The line pattern of a line-and-space pattern (1L1S) (design line width: 150 nm) was observed using a scanning electron microscope ("S-9220" manufactured by Hitachi, Ltd.). The nano edge roughness was evaluated by determining a difference "ACD" between the design line width (150 nm) and the line width in an area where elevations and depressions significantly occurred along a side 2a of a line area 2 of a resist film formed on a silicon wafer 1 (see FIGS. 1 and 2) using a CD-SEM ("S-9220" manufactured by Hitachi High-Technologies Corporation). Note that elevations and depressions are exaggerated in FIGS. 1 and 2.

Resolution (L/S) (nm)

The minimum line width of a line pattern of a line-and-space pattern (1L1S) that was resolved at the optimum dose was taken as the resolution.

Synthesis Example 1

Production of Resin (A-1)

56 g of p-acetoxystyrene, 44 g of the compound shown by the following formula (M-1) (hereinafter may be referred to as "compound (M-1)"), 4 g of azobisisobutylonitrile (AIBN), and 1 g of t-dodecylmercaptan were dissolved in 100 g of propylene glycol monomethyl ether. The monomers were polymerized at 70° C. for 16 hours in a nitrogen atmosphere. After completion of polymerization, the reaction solution was added dropwise to 1000 g of n-hexane to coagulate and purify the copolymer. After the addition of 150 g of propylene glycol monomethyl ether to the copolymer, 150 g of methanol, 35 g of triethylamine, and 7 g of water were added to the mixture. The mixture was hydrolyzed for 8 hours under reflux at the boiling point. After completion of the reaction, the solvent and triethylamine were evaporated under reduced pressure. After dissolving the resulting copolymer in 150 g of acetone, the solution was added dropwise to 2000 g of water to coagulate the copolymer. A white powder thus produced was filtered, and dried overnight at 50° C. under reduced pressure. The resulting copolymer had an Mw of 11,000 and an Mw/Mn ratio of 2.0. The molar ratio of repeating units derived from p-hydroxystyrene and repeating units derived from the compound (M-1) determined by $^{13}$C-NMR analysis was 65:35. The copolymer is referred to as "resin (A-1)".

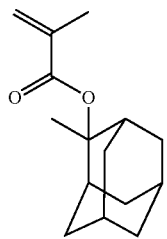

(M-1)

Synthesis Example 2

Production of Resin (A-2)

55 g of p-acetoxystyrene, 45 g of the compound shown by the following formula (M-2) (hereinafter may be referred to as "compound (M-2)"), 4 g of AIBN, and 1 g of t-dodecylmercaptan were dissolved in 100 g of propylene glycol monomethyl ether. The monomers were polymerized at 70° C. for 16 hours in a nitrogen atmosphere. After completion of polymerization, the reaction solution was added dropwise to 1000 g of n-hexane to coagulate and purify the copolymer. After the addition of 150 g of propylene glycol monomethyl ether to the copolymer, 150 g of methanol, 34 g of triethylamine, and 6 g of water were added to the mixture. The mixture was hydrolyzed for 8 hours under reflux at the boiling point. After completion of the reaction, the solvent and triethylamine were evaporated under reduced pressure. After dissolving the resulting copolymer in 150 g of acetone, the solution was added dropwise to 2000 g of water to coagulate the copolymer. A white powder thus produced was filtered, and dried overnight at 50° C. under reduced pressure. The resulting copolymer had an Mw of 10,000 and an Mw/Mn ratio of 2.1. The molar ratio of repeating units derived from p-hydroxystyrene and repeating units derived from the compound (M-2) determined by $^{13}$C-NMR analysis was 65:35. The copolymer is referred to as "resin (A-2)".

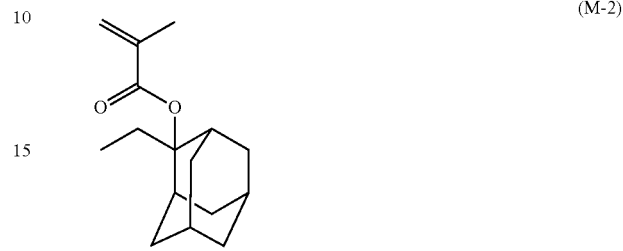

(M-2)

Example 1

100 parts of the resin (A-1) produced in Synthesis Example 1, 15 parts of an acid generator (B-1), 5 parts of a carboxylic acid generator (C-1), 2 parts of an acid diffusion controller (D-1), 1100 parts of a solvent (E-1), and 2500 parts of a solvent (E-2) were mixed. The mixture was filtered through a membrane filter (pore size: 200 nm) to obtain a composition solution of a radiation-sensitive resin composition.

Examples 2 to 5 and Comparative Examples 1 to 3

The resin (A), the acid generator (B), the carboxylic acid generator (C), the acid diffusion controller (D), and the solvent (E) were mixed in a ratio shown in Table 1. The mixture was filtered through a membrane filter (pore size: 200 nm) to obtain a composition solution of a radiation-sensitive resin composition.

TABLE 1

| | Resin (A) | | Acid generator (B) | | Carboxylic acid generator (C) | | Acid diffusion controller (D) | | Solvent (E) | |
|---|---|---|---|---|---|---|---|---|---|---|
| | Type | Amount (parts) | Type | Amount (parts) | Type | Amount (parts) | Type | Amount (parts) | Type | Amount (parts) |
| Example 1 | A-1 | 100 | B-1 | 15 | C-1 | 5 | D-1 | 2 | E-1 | 1100 |
| | | | | | | | | | E-2 | 2500 |
| Example 2 | A-1 | 100 | B-1 | 15 | C-1 | 5 | — | — | E-1 | 1100 |
| | | | | | | | | | E-2 | 2500 |
| Example 3 | A-1 | 100 | B-2 | 15 | C-1 | 5 | — | — | E-1 | 1100 |
| | | | | | | | | | E-2 | 2500 |
| Example 4 | A-2 | 100 | B-1 | 15 | C-1 | 5 | D-1 | 2 | E-1 | 1100 |
| | | | | | | | | | E-2 | 2500 |
| Example 5 | A-1 | 100 | B-1 | 15 | C-3 | 5 | — | — | E-1 | 1100 |
| | | | | | | | | | E-2 | 2500 |
| Comparative Example 1 | A-1 | 100 | B-1 | 15 | — | — | D-1 | 2 | E-1 | 1100 |
| | | | | | | | | | E-2 | 2500 |
| Comparative Example 2 | A-1 | 100 | B-1 | 15 | C-2 | 5 | — | — | E-1 | 1100 |
| | | | | | | | | | E-2 | 2500 |
| Comparative Example 3 | A-1 | 100 | B-1 | 15 | C-2 | 5 | D-1 | 2 | E-1 | 1100 |
| | | | | | | | | | E-2 | 2500 |

The details of the acid generator (B), the carboxylic acid generator (C), the acid diffusion controller (D), and the solvent (E) are given below.

Acid Generator (B)
(B-1): compound shown by formula (B-1)
(B-2): compound shown by formula (B-2)

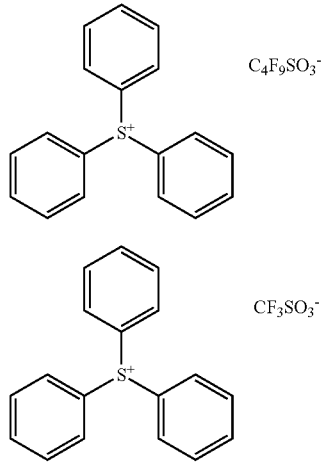

Carboxylic Acid Generator (C)
(C-1): compound shown by formula (C-1)
(C-2): compound shown by formula (C-2)
(C-3): compound shown by formula (C-3)

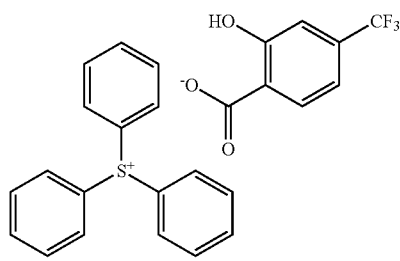

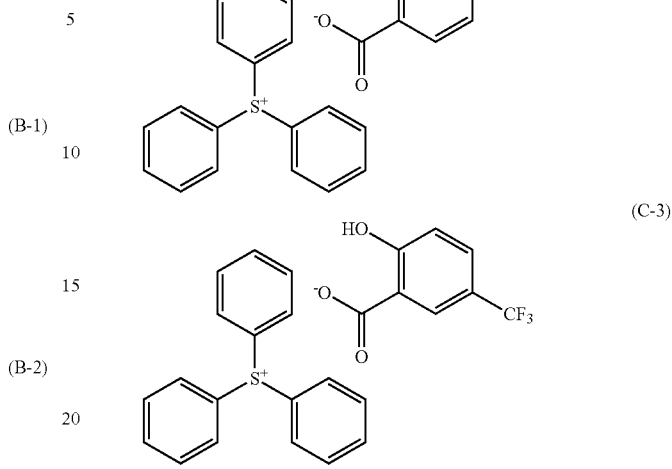

Acid diffusion Controller (D)
(D-1): tri-n-octylamine
Solvent (E)
(E-1): ethyl lactate
(E-2): propylene glycol monomethyl ether acetate Evaluation of Radiation-Sensitive Resin Composition The composition solution of the radiation-sensitive resin composition was spin-coated onto a silicon wafer using a semiconductor production system "CLEAN TRACK ACT-8" (manufactured by Tokyo Electron, Ltd.), and pre-baked (PB) under conditions shown in Table 2 to form a resist film having a thickness of 50 nm. The resist film was exposed to electron beams using an electron beam drawing system ("HL800D" manufactured by Hitachi, Ltd., output: 50 KeV, current density: 5.0 A/cm$^2$). Next, the resist film was subjected to post-exposure bake (PEB) under conditions shown in Table 2. The resist film was then developed at 23° C. for 1 minute by a puddle method using a 2.38% tetramethylammonium hydroxide aqueous solution, washed with purified water, and dried to obtain a resist pattern. The resulting resist pattern was evaluated as described above. The evaluation results are shown in Table 2.

TABLE 2

| | PB conditions | | PEB conditions | | Sensitivity | Nano edge | Resolution |
| --- | --- | --- | --- | --- | --- | --- | --- |
| | Temperature (° C.) | Time (sec) | Temperature (° C.) | Time (sec) | ($\mu$C/cm$^2$) | roughness (nm) | (nm) |
| Example 1 | 110 | 60 | 110 | 60 | 22 | 10 | 90 |
| Example 2 | 110 | 60 | 110 | 60 | 16 | 11 | 90 |
| Example 3 | 110 | 60 | 110 | 60 | 15 | 10 | 80 |
| Example 4 | 110 | 60 | 110 | 60 | 20 | 10 | 80 |
| Example 5 | 110 | 60 | 110 | 60 | 17 | 12 | 90 |
| Comparative Example 1 | 110 | 60 | 110 | 60 | 31 | 20 | 150 |
| Comparative Example 2 | 110 | 60 | 110 | 60 | 28 | 20 | 140 |
| Comparative Example 3 | 110 | 60 | 110 | 60 | 40 | 18 | 130 |

As shown in Table 2, it was confirmed that a chemically-amplified positive-tone resist film that effectively responds to electron beams or extreme ultraviolet rays, exhibits low roughness and excellent sensitivity, and can accurately and stably form a fine pattern, can be formed using the radiation-sensitive resin compositions of Examples 1 to 5 including the carboxylic acid generator (C-1) or (C-3) as compared with the case of using the radiation-sensitive resin composition of Comparative Example 1 that did not include the carboxylic acid generator (C). It was also confirmed that a chemically-amplified positive-tone resist film that exhibits low roughness and excellent sensitivity, and can accurately and stably form a fine pattern, can be formed using the radiation-sensitive resin compositions of Examples 1 to 5 including the carboxylic acid generator (C-1) or (C-3) as compared with the radiation-sensitive resin compositions of Comparative Examples 2 and 3 including the carboxylic acid generator (C-2).

In Examples 6 to 19 and Comparative Examples 4 to 6, an evaluation substrate was produced and evaluated by the following methods.

Specifically, a lower-layer antireflective film composition ("ARC66" manufactured by Brewer Science) was spin-coated onto a 12-inch silicon wafer using a coater/developer ("CLEAN TRACK ACT12" manufactured by Tokyo Electron Ltd.), and pre-baked (PB) at 205° C. for 60 seconds to form a film (thickness: 105 nm). The radiation-sensitive resin composition (described later) was spin-coated onto the film using the coater/developer, baked under conditions shown in Table 6, and cooled at 23° C. for 30 seconds to form a coating film (thickness: 80 nm).

The coating film was exposed via a mask (48 nm line/2×48 nm pitch) using an ArF liquid immersion lithography system ("NSR-S610C" manufactured by Nikon Corporation) (NA: 1.30). The coating film was then subjected to PEB on a hot plate of a semiconductor production system ("CLEAN TRACK LITHIUS PROI" manufactured by Tokyo Electron Ltd.), cooled at 23° C. for 30 seconds, subjected to puddle development (10 sec) using a 2.38% tetramethylammonium hydroxide aqueous solution (using the GP nozzle of the development cup), and rinsed with ultrapure water. The wafer was then spin-dried at 2000 rpm for 15 seconds to obtain an evaluation substrate on which a resist pattern was formed.

Sensitivity (L/S) (mJ/cm²)

A dose at which a line-and-space pattern (1L1S) including a line area (width: 48 nm) and a space area (groove) (width: 48 nm) defined by the adjacent line areas was formed at a line width of 1:1 was defined as an optimum dose, and the sensitivity was evaluated based on the optimum dose.

Line Width Roughness (LWR)

A 48 nm line-and-space pattern resolved at the optimum dose was observed from above using a scanning electron microscope ("CG-4000" manufactured by Hitachi High-Technologies Corporation). The line width was measured at arbitrary points, and a variation in measured values was indicated by 3σ (nm). A case where the LWR was less than 7 nm was evaluated as "Acceptable", and a case where the LWR was 7 nm or more was evaluated as "Unacceptable".

Pattern Shape

The cross-sectional shape of the 48 nm line-and-space pattern of the resist film formed when evaluating the sensitivity was observed using the above scanning electron microscope, and the line width Lb in an intermediate area of the resist pattern and the line width La at the top of the resist film were measured. A case where the value "La/Lb" was within the range of "0.9≤La/Lb≤1.1" was evaluated as "Acceptable", and a case where the value "La/Lb" was outside the range of "0.9≤La/Lb≤1.1" was evaluated as "Unacceptable".

Minimum Pre-Collapse Dimension

The resist film was sequentially exposed at a dose higher than the optimum dose. In such a case, the line width of the resulting pattern gradually decreases, and the resist pattern collapses when the resist pattern has a line width corresponding to a given dose. A line width at the maximum dose at which the resist pattern does not collapse was defined as the minimum pre-collapse dimension (nm). The minimum pre-collapse dimension was used as an index of the pattern collapse resistance. The minimum pre-collapse dimension was measured using the above scanning electron microscope. A resist film is determined to have excellent properties when the line width is small. A case where the minimum pre-collapse dimension was less than 40 nm was evaluated as "Acceptable", and a case where the minimum pre-collapse dimension was 40 nm or more was evaluated as "Unacceptable".

The following compounds ((M-1) to (M-10)) were used in Synthesis Examples 3 to 15.

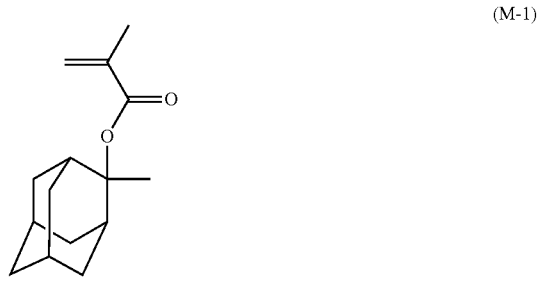

(M-1)

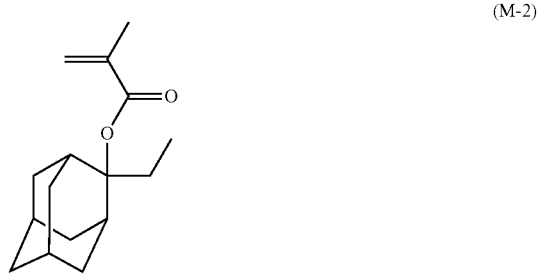

(M-2)

(M-3)

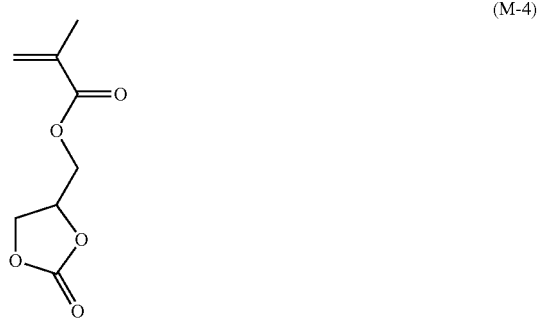

(M-4)

-continued (M-5)
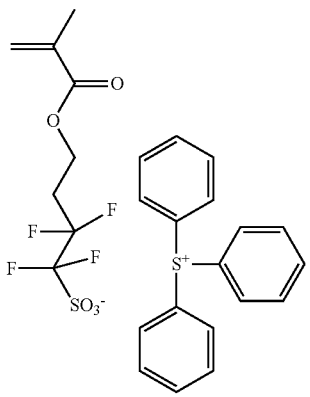

(M-6)
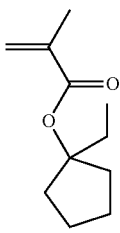

(M-7)
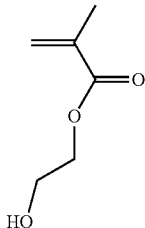

(M-8)
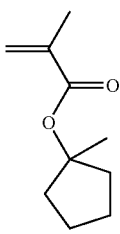

(M-9)
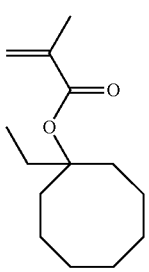

(M-10)
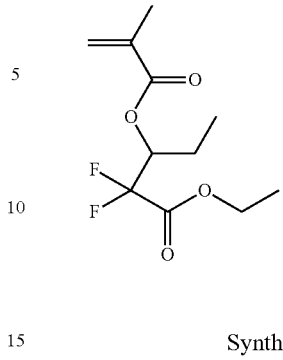

Synthesis Example 3

Production of Resin (A-3)

50.4 g (50 mol %) of the compound shown by the formula (M-3) (compound (M-3)), 12.4 g (15 mol %) of the compound shown by the formula (M-6) (compound (M-6)), and 37.2 g (35 mol %) of the compound shown by the formula (M-1) (compound (M-1)) were dissolved in 200 g of 2-butanone to prepare a solution. 7.45 g of AIBN was added to the solution to prepare a monomer solution.

A 1000 ml three-necked flask charged with 100 g of 2-butanone was purged with nitrogen for 30 minutes. The flask was then heated to 80° C. with stirring, and the monomer solution was added dropwise to the flask using a dropping funnel over 3 hours. The monomers were polymerized for 6 hours from the start of addition of the monomer solution to obtain a polymer solution. After completion of polymerization, the polymer solution was cooled with water to 30° C. or less, and added to 2000 g of methanol to precipitate a white substance. The white substance was collected by filtration, and washed with 800 g of methanol. The white substance was then collected again by filtration, and dried at 50° C. for 17 hours to obtain a white powder (copolymer) (60.2 g, yield: 60%).

The copolymer had a weight average molecular weight (Mw) of 4100 and an Mw/Mn ratio of 1.12. The molar ratio of repeating units derived from the compounds (M-3), (M-6), and (M-1) determined by $^{13}$C-NMR analysis was 51.2:14.6:34.2. The copolymer is referred to as "resin (A-3)".

Synthesis Examples 4 to 6

Production of Resins (A-4) to (A-6)

A copolymer was obtained in the same manner as in Synthesis Example 3, except for changing the components as shown in Table 3. The amount and the yield of each copolymer (resins (A-4) to (A-6)) are also shown in Table 3. The property values of each resin are shown in Table 4.

Synthesis Example 7

31.6 g (35 mol %) of the compound shown by the formula (M-6) (compound (M-6)), 6.5 g (10 mol %) of the compound shown by the formula (M-7) (compound (M-7)), and 45.83 g (45 mol %) of the compound shown by the formula (M-3) (compound (M-3)) were dissolved in 200 g of 2-butanone to prepare a solution. 8.1 g of AIBN was added to the solution to prepare a monomer solution.

A 1000 ml three-necked flask charged with 12.3 g (10 mol %) of the compound shown by the formula (M-2) (compound (M-2)) and 100 g of 2-butanone was purged with nitrogen for 30 minutes. The flask was then heated to 80° C. with stirring, and the monomer solution was added dropwise to the flask using a dropping funnel over 3 hours. The monomers were polymerized for 6 hours from the start of addition of the monomer solution to obtain a polymer solution. After completion of polymerization, the polymer solution was cooled with water to 30° C. or less, and added to 2000 g of methanol to precipitate a white substance. The white substance was collected by filtration, and washed with 800 g of methanol. The white substance was then collected again by filtration, and dried at 50° C. for 17 hours to obtain a white powder (copolymer) (63.0 g, yield: 63%).

The copolymer had a weight average molecular weight (Mw) of 3900 and an Mw/Mn ratio of 1.28. The molar ratio of repeating units derived from the compounds (M-6), (M-7), (M-3, and (M-2) determined by $^{13}$C-NMR analysis was 35.5: 10.0:45.2:9.3. The copolymer is referred to as "resin (A-7)".

Synthesis Example 8

Production of Resin (A-8)

A copolymer was obtained in the same manner as in Synthesis Example 3, except for changing the components as shown in Table 3. The amount and the yield of the copolymer (resin (A-8)) are also shown in Table 3. The property values of the resin are shown in Table 4.

Synthesis Examples 9 and 10

Production of Resins (A-9) and (A-10)

A copolymer was obtained in the same manner as in Synthesis Example 7, except for changing the components as shown in Table 3. The amount and the yield of each copolymer (resins (A-9) and (A-10)) are also shown in Table 3. The property values of each resin are shown in Table 4.

Synthesis Example 11

Production of Resin (A-11)

A copolymer was obtained in the same manner as in Synthesis Example 3, except for changing the components as shown in Table 3. The amount and the yield of the copolymer (resin (A-11)) are also shown in Table 3. The property values of the resin are shown in Table 4.

Synthesis Examples 12 to 14

Production of Resins (A-12) to (A-14)

A copolymer was obtained in the same manner as in Synthesis Example 7, except for changing the components as shown in Table 3. The amount and the yield of each copolymer (resins (A-12) to (A-14)) are also shown in Table 3. The property values of each resin are shown in Table 4.

Synthesis Example 15

Production of Resin Additive (F-1)

37.4 g (40 mol %) of the compound shown by the formula (M-9) (compound (M-9)) and 62.6 g (60 mol %) of the compound shown by the formula (M-10) (compound (M-10)) were dissolved in 100 g of 2-butanone to prepare a solution. 4.8 g of dimethyl-2,2'-azobisisobutyrate was added to the solution to prepare a monomer solution.

A 500 ml three-necked flask charged with 100 g of 2-butanone was purged with nitrogen for 30 minutes. The flask was then heated to 80° C. with stirring, and the monomer solution was added dropwise to the flask using a dropping funnel over 3 hours. The monomers were polymerized for 6 hours from the start of addition of the monomer solution to obtain a polymer solution. After completion of polymerization, the polymer solution was cooled with water to 30° C. or less, and added to 800 g of a methanol-water mixture (methanol/water=19/1 (volume ratio)) to precipitate a white substance. After removing the supernatant liquid, the white substance was washed with 800 g of a methanol-water mixture. The solvent was then replaced with propylene glycol monomethyl ether acetate to obtain a resin solution (47.0 g (solid), yield: 47%).

The copolymer had a weight average molecular weight (Mw) of 4000 and an Mw/Mn ratio of 1.35. The molar ratio of repeating units derived from the compounds (M-9) and (M-10) determined by $^{13}$C-NMR analysis was 40.2:59.8. The copolymer is referred to as "resin additive (F-1)".

TABLE 3

| | Monomer | | | | | | | | Azobisisobutyronitrile | Resin | | |
|---|---|---|---|---|---|---|---|---|---|---|---|---|
| | Type | Amount (mol %) | Type | Amount (mol %) | Type | Amount (mol %) | Type | Amount (mol %) | Amount (g) | Type | Amount (g) | Yield (%) |
| Synthesis Example 3 | M-3 | 50 | M-6 | 15 | M-1 | 35 | — | — | 7.45 | (A-3) | 60.2 | 60 |
| Synthesis Example 4 | M-3 | 20 | M-6 | 15 | M-1 | 45 | M-4 | 20 | 7.66 | (A-4) | 62.3 | 62 |
| Synthesis Example 5 | M-3 | 20 | M-8 | 15 | M-1 | 45 | M-4 | 20 | 7.73 | (A-5) | 61.2 | 61.2 |
| Synthesis Example 6 | M-3 | 51 | M-6 | 46 | M-5 | 3 | — | — | 3.84 | (A-6) | 68.3 | 68 |
| Synthesis Example 7 | M-6 | 35 | M-7 | 10 | M-3 | 45 | M-2 | 10 | 8.1 | (A-7) | 63.0 | 63 |
| Synthesis Example 8 | M-8 | 50 | M-3 | 50 | — | — | — | — | 4.2 | (A-8) | 69.2 | 69 |
| Synthesis Example 9 | M-6 | 40 | M-7 | 5 | M-3 | 45 | M-2 | 10 | 8.0 | (A-9) | 60.5 | 61 |

TABLE 3-continued

| | Monomer | | | | | | | | Resin | |
|---|---|---|---|---|---|---|---|---|---|---|---|
| | Type | Amount (mol %) | Type | Amount (mol %) | Type | Amount (mol %) | Type | Amount (mol %) | Azobisisobutyronitrile Amount (g) | Type | Amount (g) | Yield (%) |
| Synthesis Example 10 | M-6 | 40 | M-3 | 50 | M-2 | 10 | — | — | 7.9 | (A-10) | 62.1 | 62 |
| Synthesis Example 11 | M-6 | 50 | M-3 | 50 | — | — | — | — | 4.1 | (A-11) | 66.4 | 66 |
| Synthesis Example 12 | M-6 | 30 | M-7 | 10 | M-3 | 50 | M-2 | 10 | 10.8 | (A-12) | 64.2 | 64 |
| Synthesis Example 13 | M-6 | 38 | M-7 | 10 | M-3 | 45 | M-2 | 7 | 8.0 | (A-13) | 60.2 | 60 |
| Synthesis Example 14 | M-6 | 40 | M-7 | 10 | M-3 | 40 | M-2 | 10 | 8.2 | (A-14) | 61.3 | 61 |
| Synthesis Example 15 | M-9 | 40 | M-10 | 60 | — | — | — | — | 4.8*[1] | (F-1) | 47.0 | 47 |

*[1]Dimethyl-2,2'-azobisisobutyrate

TABLE 4

| | Resin | | | Repeating unit | | | | | | | |
|---|---|---|---|---|---|---|---|---|---|---|---|
| | Type | Mw | Mw/Mn | Type | Content (mol %) | Type | Content (mol %) | Type | Content (mol %) | Type | Content (mol %) |
| Synthesis Example 3 | (A-3) | 4100 | 1.12 | M-3 | 51.2 | M-6 | 14.6 | M-1 | 34.2 | — | — |
| Synthesis Example 4 | (A-4) | 3600 | 1.25 | M-3 | 21.0 | M-6 | 14.8 | M-1 | 44.2 | M-4 | 20.0 |
| Synthesis Example 5 | (A-5) | 3700 | 1.27 | M-3 | 21.8 | M-8 | 14.6 | M-1 | 44.4 | M-4 | 19.2 |
| Synthesis Example 6 | (A-6) | 6100 | 1.28 | M-3 | 51.2 | M-6 | 45.8 | M-5 | 3.0 | — | — |
| Synthesis Example 7 | (A-7) | 3900 | 1.28 | M-6 | 35.5 | M-7 | 10.0 | M-3 | 45.2 | M-2 | 9.3 |
| Synthesis Example 8 | (A-8) | 6400 | 1.47 | M-8 | 47.8 | M-3 | 52.2 | — | — | — | — |
| Synthesis Example 9 | (A-9) | 3800 | 1.26 | M-6 | 40.5 | M-7 | 4.8 | M-3 | 45.2 | M-2 | 9.5 |
| Synthesis Example 10 | (A-10) | 4100 | 1.29 | M-6 | 39.5 | M-3 | 51.8 | M-2 | 8.7 | — | — |
| Synthesis Example 11 | (A-11) | 6200 | 1.44 | M-6 | 48.6 | M-3 | 51.4 | — | — | — | — |
| Synthesis Example 12 | (A-12) | 3800 | 1.24 | M-6 | 29.8 | M-7 | 9.8 | M-3 | 51.0 | M-2 | 9.4 |
| Synthesis Example 13 | (A-13) | 3700 | 1.23 | M-6 | 36.5 | M-7 | 7.8 | M-3 | 45.6 | M-2 | 10.1 |
| Synthesis Example 14 | (A-14) | 3800 | 1.26 | M-6 | 38.5 | M-7 | 9.6 | M-3 | 42.5 | M-2 | 9.4 |
| Synthesis Example 15 | (F-1) | 4000 | 1.35 | M-9 | 40.2 | M-10 | 59.8 | — | — | — | — |

Examples 6 to 19 and Comparative Examples 4 to 6

The components shown in Table 5 were mixed, and filtered through a filter having a pore size of 0.05 μm to obtain a radiation-sensitive resin composition (Examples 6 to 19 and Comparative Examples 4 to 6). The radiation-sensitive resin composition was evaluated as described above. The evaluation results are shown in Table 6.

The details of the acid generator (B), the carboxylic acid generator (C), the acid diffusion controller (D), and the solvent (E) shown in Table 5 are given below.

Acid Generator (B)
(B-3): compound shown by formula (B-3)
(B-4): compound shown by formula (B-4)

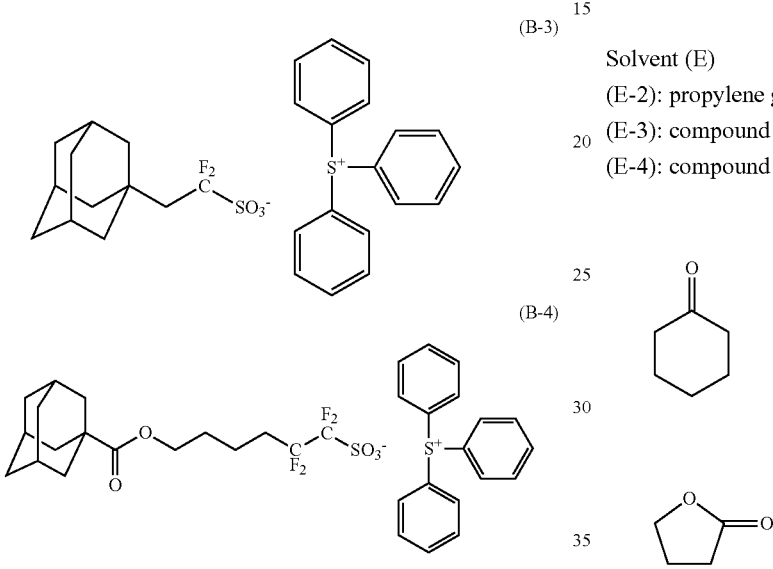

Carboxylic Acid Generator (C)
(C-1): compound shown by formula (C-1)
(C-2): compound shown by formula (C-2)
(C-3): compound shown by formula (C-3)
Acid Diffusion Controller (D)
(D-2): compound shown by formula (D-2) (N-t-butoxycarbonyl-4-hydroxypiperidine)

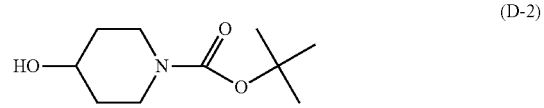

Solvent (E)
(E-2): propylene glycol monomethyl ether acetate
(E-3): compound shown by formula (E-3) (cyclohexanone)
(E-4): compound shown by formula (E-4) (γ-butyrolactone)

TABLE 5

| | Resin (A) | | Acid generator (B) | | Carboxylic acid generator (C) | | Acid diffusion controller (D) | | Resin additive (F) | | Solvent (E) | | | | | |
|---|---|---|---|---|---|---|---|---|---|---|---|---|---|---|---|---|
| | Type | Amount (parts) | Type | Amount (parts) | Type | Amount (parts) | Type | Amount (parts) | Type | Amount (parts) | Type | Amount (parts) | Type | Amount (parts) | Type | Amount (parts) |
| Example 6 | A-3 | 100 | B-3 | 8 | C-1 | 2.1 | — | — | — | — | E-2 | 2000 | E-3 | 850 | E-4 | 30 |
| Example 7 | A-4 | 100 | B-3 | 8 | C-1 | 2.1 | — | — | — | — | E-2 | 2000 | E-3 | 850 | E-4 | 30 |
| Example 8 | A-5 | 100 | B-3 | 8 | C-1 | 2.1 | — | — | — | — | E-2 | 2000 | E-3 | 850 | E-4 | 30 |
| Example 9 | A-6 | 100 | — | — | C-1 | 4.1 | — | — | — | — | E-2 | 2000 | E-3 | 850 | E-4 | 30 |
| Example 10 | A-7 | 100 | B-4 | 14 | C-1 | 9.6 | — | — | F-1 | 3 | E-2 | 2620 | E-3 | 1125 | E-4 | 200 |
| Example 11 | A-7 | 100 | B-4 | 14 | C-1 | 6.7 | — | — | F-1 | 3 | E-2 | 2620 | E-3 | 1125 | E-4 | 200 |
| Example 12 | A-7 | 100 | B-4 | 13 | C-1 | 7.1 | — | — | F-1 | 3 | E-2 | 2620 | E-3 | 1125 | E-4 | 200 |
| Example 13 | A-7 | 100 | B-4 | 12 | C-1 | 8.2 | — | — | F-1 | 3 | E-2 | 2620 | E-3 | 1125 | E-4 | 200 |
| Example 14 | A-8 | 100 | B-4 | 10.8 | C-1 | 7.4 | — | — | F-1 | 3 | E-2 | 2620 | E-3 | 1125 | E-4 | 200 |
| Example 15 | A-9 | 100 | B-4 | 12 | C-1 | 8.2 | — | — | F-1 | 3 | E-2 | 2620 | E-3 | 1125 | E-4 | 200 |
| Example 16 | A-10 | 100 | B-4 | 12 | C-1 | 8.2 | — | — | F-1 | 3 | E-2 | 2620 | E-3 | 1125 | E-4 | 200 |
| Example 17 | A-11 A-12 | 50 50 | B-4 | 13 | C-1 | 8.9 | — | — | F-1 | 3 | E-2 | 2620 | E-3 | 1125 | E-4 | 200 |
| Example 18 | A-13 | 100 | B-4 | 13 | C-1 | 8.9 | — | — | F-1 | 3 | E-2 | 2620 | E-3 | 1125 | E-4 | 200 |
| Example 19 | A-14 | 100 | B-4 | 13 | C-1 | 8.9 | — | — | F-1 | 3 | E-2 | 2620 | E-3 | 1125 | E-4 | 200 |
| Comparative Example 4 | A-3 | 100 | B-3 | 8 | — | — | D-2 | 0.65 | — | — | E-2 | 2620 | E-3 | 1125 | E-4 | 200 |
| Comparative Example 5 | A-5 | 100 | B-3 | 8 | — | — | D-2 | 0.65 | — | — | E-2 | 2620 | E-3 | 1125 | E-4 | 200 |
| Comparative Example 6 | A-7 | 100 | B-4 | 14 | — | — | D-2 | 1.45 | F-1 | 3 | E-2 | 2620 | E-3 | 1125 | E-4 | 200 |

TABLE 6

| | PB | | PEB | | Sensitivity | Line width roughness | Pattern shape | Minimum pre-collapse dimension |
| --- | --- | --- | --- | --- | --- | --- | --- | --- |
| | Temperature (° C.) | Time (sec) | Temperature (° C.) | Time (sec) | (mJ/m$^2$) | (LWR) | | |
| Example 6 | 100 | 60 | 105 | 60 | 40 | Acceptable | Acceptable | Acceptable |
| Example 7 | 100 | 60 | 95 | 60 | 41 | Acceptable | Acceptable | Acceptable |
| Example 8 | 100 | 60 | 95 | 60 | 40 | Acceptable | Acceptable | Acceptable |
| Example 9 | 100 | 60 | 150 | 60 | 41 | Acceptable | Acceptable | Acceptable |
| Example 10 | 120 | 60 | 85 | 60 | 43 | Acceptable | Acceptable | Acceptable |
| Example 11 | 120 | 60 | 85 | 60 | 45 | Acceptable | Acceptable | Acceptable |
| Example 12 | 120 | 60 | 85 | 60 | 42 | Acceptable | Acceptable | Acceptable |
| Example 13 | 120 | 60 | 85 | 60 | 44 | Acceptable | Acceptable | Acceptable |
| Example 14 | 120 | 60 | 105 | 60 | 41 | Acceptable | Acceptable | Acceptable |
| Example 15 | 120 | 60 | 85 | 60 | 42 | Acceptable | Acceptable | Acceptable |
| Example 16 | 120 | 60 | 85 | 60 | 43 | Acceptable | Acceptable | Acceptable |
| Example 17 | 120 | 60 | 85 | 60 | 44 | Acceptable | Acceptable | Acceptable |
| Example 18 | 120 | 60 | 85 | 60 | 45 | Acceptable | Acceptable | Acceptable |
| Example 19 | 120 | 60 | 85 | 60 | 43 | Acceptable | Acceptable | Acceptable |
| Comparative Example 4 | 100 | 60 | 105 | 60 | 56 | Unacceptable | Unacceptable | Unacceptable |
| Comparative Example 5 | 100 | 60 | 95 | 60 | 54 | Unacceptable | Unacceptable | Unacceptable |
| Comparative Example 6 | 100 | 60 | 85 | 60 | 45 | Unacceptable | Unacceptable | Unacceptable |

As shown in Table 6, it was confirmed that a chemically-amplified positive-tone resist film that effectively responds to ArF excimer laser light, exhibits low line width roughness, excellent sensitivity, and an excellent pattern shape, can accurately and stably form a fine pattern, and exhibits excellent pattern collapse resistance (small minimum pre-collapse dimension), can be formed using the radiation-sensitive resin compositions of Examples 6 to 19 including the carboxylic acid generator (C-1) as compared with the case of using the radiation-sensitive resin compositions of Comparative Examples 4 to 6 that did not include the carboxylic acid generator (C).

Since the radiation-sensitive resin composition according to the embodiments of the invention exhibits high resolution when forming a line-and-space pattern and exhibits low nano edge roughness, the radiation-sensitive resin composition may be useful when forming a fine pattern using ArF excimer laser light, EB, EUV, or X-rays. Therefore, the radiation-sensitive resin composition may be very useful as a material for forming a chemically-amplified resist for producing semiconductor devices that are expected to be further scaled down in the future.

Obviously, numerous modifications and variations of the present invention are possible in light of the above teachings. It is therefore to be understood that within the scope of the appended claims, the invention may be practiced otherwise than as specifically described herein.

The invention claimed is:

1. A radiation-sensitive resin composition comprising:
an acid-dissociable group-containing resin; and
a compound shown by a general formula (1), $$M^+Z^- \qquad (1)$$

wherein $Z^-$ represents a monovalent anion shown by a general formula (2), and $M^+$ represents a monovalent onium cation,

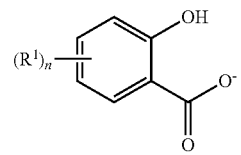

(2)

wherein $R^1$ represents a linear or branched alkyl group having 1 to 12 carbon atoms unsubstituted or substituted with a fluorine atom, or a linear or branched alkoxy group having 1 to 12 carbon atoms, and n is 1 or 2.

2. The radiation-sensitive resin composition according to claim 1, further comprising a photoacid generator that generates an acid having a pKa of 2 or less upon exposure to radiation.

3. The radiation-sensitive resin composition according to claim 2, wherein the photoacid generator is a sulfonic acid generator that generates a sulfonic acid upon exposure to radiation.

4. The radiation-sensitive resin composition according to claim 1, wherein the acid-dissociable group-containing resin comprises at least one of a repeating unit shown by a general formula (3), a repeating unit shown by a general formula (4), and a repeating unit shown by a general formula (5),

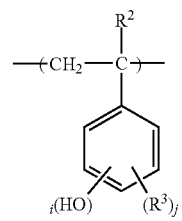

(3)

wherein $R^2$ represents a hydrogen atom or a methyl group, $R^3$ represents a hydrogen atom, a linear or branched alkyl group having 1 to 12 carbon atoms, or a linear or branched alkoxy group having 1 to 12 carbon atoms, i is an integer from 0 to 3, and j is an integer from 0 to 3,

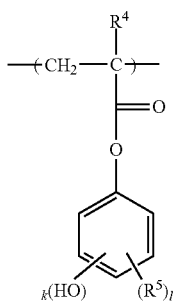

(4)

wherein $R^4$ represents a hydrogen atom or a methyl group, $R^5$ represents a hydrogen atom, a linear or branched alkyl group having 1 to 12 carbon atoms, or a linear or branched alkoxy group having 1 to 12 carbon atoms, k is an integer from 1 to 3, and l is an integer from 0 to 3,

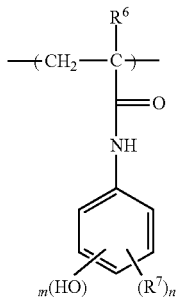

(5)

wherein $R^6$ represents a hydrogen atom or a methyl group, $R^7$ represents a hydrogen atom, a linear or branched alkyl group having 1 to 12 carbon atoms, or a linear or branched alkoxy group having 1 to 12 carbon atoms, m is an integer from 1 to 3, and n is an integer from 0 to 3.

5. The radiation-sensitive resin composition according to claim 1, wherein the acid-dissociable group-containing resin comprises a repeating unit shown by a general formula (6),

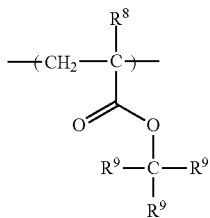

(6)

wherein
  $R^8$ represents a hydrogen atom, a methyl group, a trifluoromethyl group, or a hydroxymethyl group, and
  each $R^9$ independently represents a monovalent alicyclic hydrocarbon group having 4 to 20 carbon atoms, a derivative of the monovalent alicyclic hydrocarbon group having 4 to 20 carbon atoms, or a linear or branched alkyl group having 1 to 4 carbon atoms, and each $R^9$ is a same as or different from each other, or
  each $R^9$ independently represents a monovalent alicyclic hydrocarbon group having 4 to 20 carbon atoms, a derivative of the monovalent alicyclic hydrocarbon group having 4 to 20 carbon atoms, or a linear or branched alkyl group having 1 to 4 carbon atoms, each $R^9$ is a same as or different from each other, and two of $R^9$ bond to each other to form a divalent alicyclic hydrocarbon group or a derivative thereof together with the carbon atom bonded to $R^9$.

6. The radiation-sensitive resin composition according to claim 5, wherein the acid-dissociable group-containing resin further comprises at least one of a repeating unit shown by a general formula (L-1) and a repeating unit shown by a general formula (C-1),

(L-1)

wherein $R^r$ represents a hydrogen atom, a methyl group, or a trifluoromethyl group, $R^{L1}$ represents a single bond or a divalent linking group, and $R^{Lc}$ represents a monovalent organic group having a lactone structure,

(C-1)

wherein $R^r$ represents a hydrogen atom, a methyl group, or a trifluoromethyl group, $R^{C1}$ represents a single bond or a divalent linking group, and $R^{Cc}$ represents a monovalent organic group having a cyclic carbonate structure.

7. A compound shown by a general formula (1),

(1)

wherein $Z^-$ represents a monovalent anion shown by a general formula (2), and $M^+$ represents a sulfonium cation or an iodonium cation,

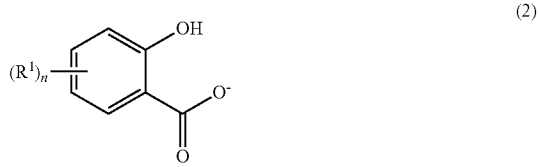

(2)

wherein $R^1$ represents a linear or branched alkyl group having 1 to 12 carbon atoms substituted with a fluorine atom, and n is 1 or 2.

* * * * *